US009573979B2

(12) United States Patent
Modrow et al.

(10) Patent No.: US 9,573,979 B2

(45) Date of Patent: Feb. 21, 2017

(54) MODIFIED VP1-CAPSID PROTEIN OF PARVOVIRUS B19

(76) Inventors: Susanne Modrow, Altenthann (DE); Torsten Lowin, Regensburg (DE); Markus Mobs, Berlin (DE); Michael Broker, Marburg (DE)

( * ) Notice: Subject to any disclaimer, the term of this patent is extended or adjusted under 35 U.S.C. 154(b) by 0 days.

(21) Appl. No.: 11/575,951

(22) PCT Filed: Sep. 23, 2005

(86) PCT No.: PCT/EP2005/054771

§ 371 (c)(1),
(2), (4) Date: Mar. 23, 2007

(87) PCT Pub. No.: WO2006/032697

PCT Pub. Date: Mar. 30, 2006

(65) Prior Publication Data

US 2007/0286870 A1 Dec. 13, 2007

(30) Foreign Application Priority Data

Sep. 24, 2004 (EP) .................................... 04450180

(51) Int. Cl.
*C07K 14/005* (2006.01)
*A61K 38/00* (2006.01)
*A61K 38/16* (2006.01)

(52) U.S. Cl.
CPC ........... *C07K 14/005* (2013.01); *A61K 38/162* (2013.01); *A61K 38/00* (2013.01); *C12N 2750/14222* (2013.01)

(58) Field of Classification Search
CPC ...... A61K 38/00; A61K 39/00; A61K 38/162; A61K 39/23; C07K 14/00; C07K 2319/00; C07K 14/015; C12N 2750/00; C12N 2750/14322
USPC ............................ 424/186.1, 192.1; 530/350
See application file for complete search history.

(56) References Cited

FOREIGN PATENT DOCUMENTS

| | | |
|---|---|---|
| WO | WO 00/30668 | 6/2000 |
| WO | WO 03/006067 | 1/2003 |

OTHER PUBLICATIONS

Zadori et al., A Viral Phospholipase A2 Is Required for Parvovirus Infectivity, Developmental Cell, 2001, 1:291-302.*
Parvovirus B19 Vaccine from MedImmune/NIH Enters Trials (from Mar. 1995 Antiviral Agents Bulletin), Antiviral Agents Bulletin (Mar. 1995), http://www.bioinfo.com/parvovirus.html.*
Woodberry et al., Immunogenicity of a Human Immunodeficiency Virus (HIV) Polytope Vaccine Containing Multiple HLA A2 HIV CD81 Cytotoxic T-Cell Epitopes, Journal of Virology, 1999, 73(7):5320-5325.*
Young et al., N Engl J Med, 2004, 350:586-597.*
Bostic et al., The Journal of Infectious Diseases, 1999, 179:619-26.*
Girod et al., "The VP1 capsid protein of adeno-associated virus type 2 is carrying a phospholipase A2 domain required for virus infectivity," *Journal of General Virology*, 83:973-978, 2002.
Grieger et al., "Surface-exposed adeno-associated virus Vp1-NLS capsid fusion protein rescues infectivity of noninfectious wild-type Vp2/Vp3 and Vp3-only capsids but not that of fivefold pore mutant virions," *Journal of Virology*, 81(15):7833-7843, 2007.
Lupescu et al., "Phospholipase A2 activity-dependent stimulation of $Ca^{2+}$ entry by human parvovirus B19 capsid protein VP1," *Journal of Virology*, 80(22):11370-11380, 2006.
Anderson et al., "An outbreak of erythema infectiosum associated with human parvovirus infection," *J. Hyg.* (London), 93(1):85-93, 1984.
Arni and Ward, "Phospholipase A2—a structural review," *Toxicon*, 34(8):827-841, 1996.
Ballou et al., "Safety and immunogenicity of a recombinant parvovirus B19 vaccine formulated with MF59C.1," *The Journal of Infectious Diseases*, 187:675-678, 2003.
Blümel et al., "Parvovirus B19 transmission by heat-treated clotting factor concentrates," *Transfusion*, 42(11):1473-1481, 2002.
Bousvaros et al., "Parvovirus B19-associated interstitial lung disease, hepatitis, and myositis," *Pediatr. Pulmonol.*, 26(5):365-369, 1998.
Brown et al., "Erythrocyte P antigen: cellular receptor for B19 parvovirus," *Science*, 262(5130):114-117,1993.
Bültmann et al., "Parvovirus B19: a pathogen responsible for more than hematologic disorders," *Virchows Arch.*, 442(1):8-17, 2003.
Cassinotti et al., "Presence and significance of human parvovirus B19 DNA in synovial membranes and bone marrow from patients with arthritis of unknown origin," *J. Med. Virol.*, 56(3):199-204, 1998.
Cervera et al., "Antiphospholipid syndrome: clinical and immunologic manifestations and patterns of disease expression in a cohort of 1,000 patients," *Arthritis Rheum.*, 46(4):1019-1027, 2002.
Cherry, "Parvovirus infections in children and adults," *Adv. Pediatr.*, 46:245-269, 1999.
Chorba et al., "The role of parvovirus B19 in aplastic crisis and erythema infectiosum (fifth disease)," *J. Infect. Dis.*, 154(3):383-393, 1986.
Cope et al., "Possible induction of systemic lupus erythematosus by human parvovirus," *Ann. Rheum. Dis.*, 51(6):803-804, 1992.
Cossart et al., "Parvovirus-like particles in human sera," *Lancet*, 1(7898):72-73, 1975.
Díaz et al., "Systemic lupus erythematosus associated with acute parvovirus B19 infection," *Clin. Microbiol. Infect.*, 8(2):115-117, 2002.
Dorsch et al., "The VP1 unique region of parvovirus B19 and its constituent phospholipase A2-like activity," *Journal of Virology*, 76(4):2014-2018, 2002.

(Continued)

*Primary Examiner* — Nicole Kinsey White
(74) *Attorney, Agent, or Firm* — Wolf, Greenfield & Sacks, P.C.

(57) ABSTRACT

The invention relates to a modified VP1-capsid protein of parvovirus B19 having a reduced phospholipase A2-like enzyme activity as compared to the wild type VP1-capsid protein of parvovirus B19 having the amino acid sequence of SeqID 1.

16 Claims, 3 Drawing Sheets

(56) References Cited

OTHER PUBLICATIONS

Figure 1:
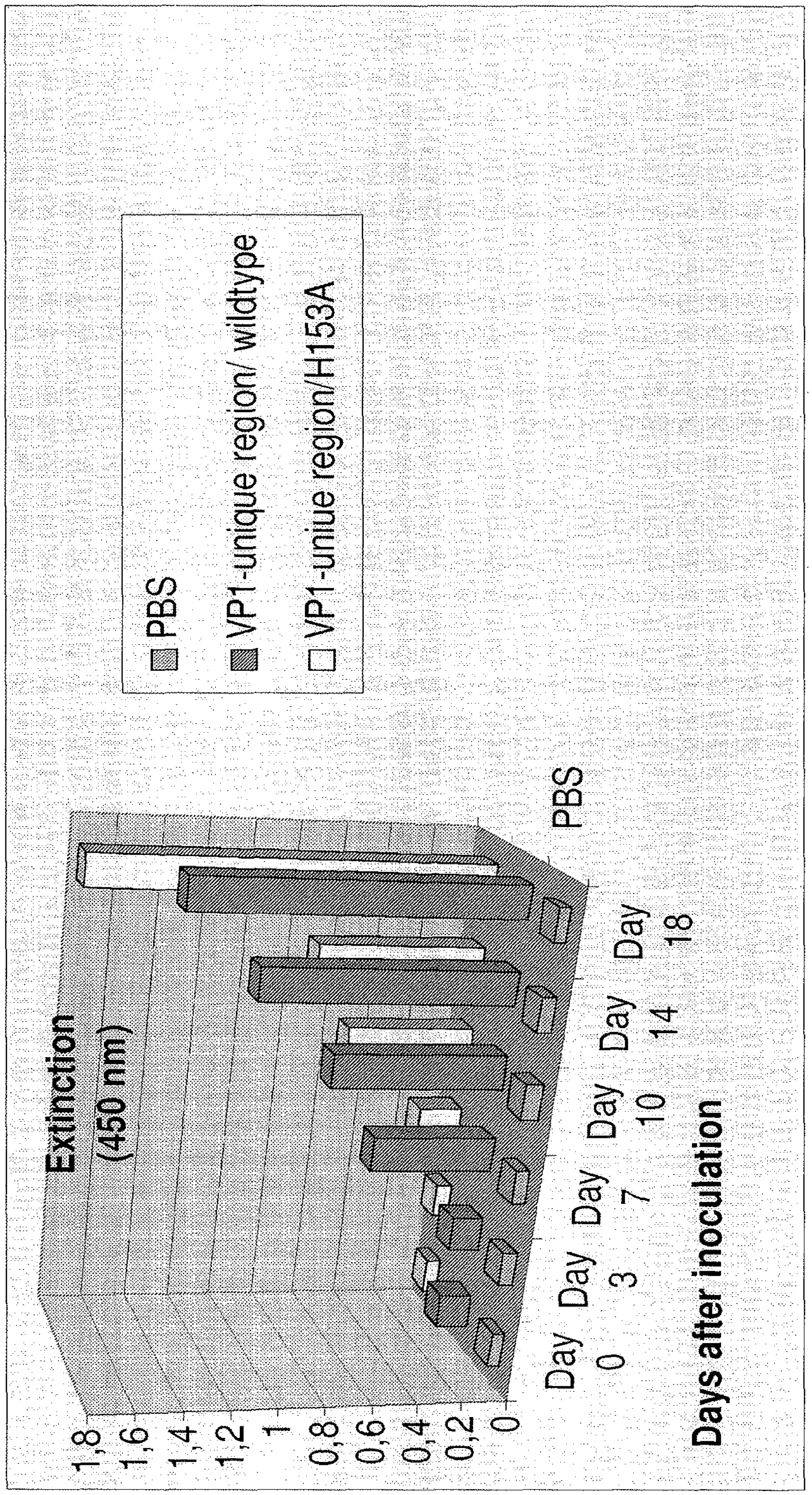

Dorsch et al., "The VP1-unique region of parvovirus B19: amino acid variability and antigenic stability," *J. Gen. Virol.*, 82(Pt 1):191-199, 2001.
Eis-Hübinger et al., "Evidence for persistence of parvovirus B19 DNA in livers of adults," *J. Med. Virol.*, 65(2):395-401, 2001.
Gigler et al., "Generation of neutralizing human monoclonal antibodies against parvovirus B19 proteins," *J. Virol.*, 73(3):1974-1979, 1999.
Hanada et al., "Childhood transient erythroblastopenia complicated by thrombocytopenia and neutropenia," *Eur. J. Haematol.*, 42(1):77-80, 1989.
Hayakawa et al., "Life-threatening human parvovirus B19 infection transmitted by intravenous immune globulin," *Br. J. Haematol.*, 118(4):1187-1189, 2002.
Heegaard and Brown, "Human parvovirus B19," *Clin. Microbiol. Rev.*, 15(3):485-505, 2002.
Hemauer et al., "Acute parvovirus B19 infection in connection with a flare of systemic lupus erythematodes in a female patient," *J. Clin. Virol.*, 14(1):73-77, 1999.
Hida et al., "Childhood idiopathic thrombocytopenic purpura associated with human parvovirus B19 infection," *J. Pediatr. Int.*, 42(6):708-710, 2000.
Ho et al., "Site-directed mutagenesis by overlap extension using the polymerase chain reaction," *Gene*, 77(1):51-59, 1989.
Hokynar et al., "Integrity and full coding sequence of B19 virus DNA persisting in human synovial tissue," *J. Gen. Virol.*, 81(Pt 4):1017-1025, 2000.
Hsu and Tsay, "Human parvovirus B19 infection in patients with systemic lupus erythematosus," *Rheumatology* (Oxford)., 40(2):152-157, 2001.
International Search Report issued in International Application No. PCT/EP2005/054771, mailed Mar. 22, 2006.
Knöll et al., "Parvovirus B19 infection in pregnancy: quantitative viral DNA analysis using a kinetic fluorescence detection system (TaqMan PCR)," *J. Med. Virol.*, 67(2):259-266, 2002.
Kurtzman et al., "Chronic bone marrow failure due to persistent B19 parvovirus infection," *N. Engl. J. Med.*, 317(5):287-294, 1987.
Langnas et al., "Parvovirus B19 as a possible causative agent of fulminant liver failure and associated aplastic anemia," *Hepatology*, 22(6):1661-1665, 1995.
Lefrère et al., "Parvovirus and idiopathic thrombocytopenic purpura," *Lancet*, 1(8632):279, 1989.
Lehmann et al., "Chronic human parvovirus B19 infection in rheumatic disease of childhood and adolescence," *J. Clin. Virol.*, 25(2):135-143, 2002.
Lehmann et al., "Frequent infection with a viral pathogen, parvovirus B19, in rheumatic diseases of childhood," *Arthritis Rheum.*, 48(6):1631-1638, 2003.
Liefeldt et al., "Recurrent high level parvovirus B19/genotype 2 viremia in a renal transplant recipient analyzed by real-time PCR for simultaneous detection of genotypes 1 to 3," *J. Med. Virol.*, 75(1):161-169, 2005.
Miller et al., "Immediate and long term outcome of human parvovirus B19 infection in pregnancy," *Br. J. Obstet. Gynaecol.*, 105(2):174-178, 1998.
Mimori et al., "Prevalence of antihuman parvovirus B19 IgG antibodies in patients with refractory rheumatoid arthritis and polyarticular juvenile rheumatoid arthritis," *Rheumatol. Int.*, 14(3):87-90, 1994.
Moore et al., "Parvovirus infection mimicking systemic lupus erythematosus in a pediatric population," *Semin. Arthritis Rheum.*, 28(5):314-318, 1999.
Moore, "Parvovirus-associated arthritis," *Curr. Opin. Rheumatol.*, 12(4):289-294, 2000.
Murai et al., "Rheumatoid arthritis after human parvovirus B19 infection," *Ann. Rheum. Dis.*, 58(2):130-132, 1999.
Murray et al., "Childhood idiopathic thrombocytopenic purpura: association with human parvovirus B19 infection," *Am. J. Pediatr. Hematol. Oncol.*, 16(4):314-319, 1994.
Naides et al., "Rheumatologic manifestations of human parvovirus B19 infection in adults. Initial two-year clinical experience," *Arthritis. Rheum.*, 33(9):1297-1309, 1990.
Negro et al., "Human parvovirus B19 infection mimicking systemic lupus erythematosus in an adult patient," *Ann. Ital. Med. Int.*, 16(2):125-127, 2001.
Nikkari et al., "Does parvovirus B19 have a role in rheumatoid arthritis?," *Ann. Rheum. Dis.*, 53(2):106-111, 1994.
Nocton et al., "Human parvovirus B19-associated arthritis in children," *J. Pediat.*, 122(2):186-190, 1993.
Nyman et al., "Detection of human parvovirus B19 infection in first-trimester fetal loss," *Obstet. Gynecol.*, 99(5 Pt 1):795-798, 2002.
Oğuz et al., "Parvovirus B19 in the acute arthropathies and juvenile rheumatoid arthritis," *J. Paediatr. Child Health*, 38(4):358-362, 2002.
Ozawa et al., "Functional mapping of the genome of the B19 (human) parvovirus by in vitro translation after negative hybrid selection," *J. Virol.*, 62(7):2508-2511, 1988.
Paver and Clarke, "Comparison of human fecal and serum parvo-like viruses," *J. Clin. Microbiol.*, 4(1):67-70, 1976.
Pont et al., "Recurrent granulocytic aplasia as clinical presentation of a persistent parvovirus B19 infection," *Br. J. Haematol.*, 80(2):160-165, 1992.
Prowse et al., "Human parvovirus B19 and blood products," *Vox Sanguinis*, 72(1):1-10, 1997.
Rogers et al., "Detection of human parvovirus B19 in early spontaneous abortuses using serology, histology, electron microscopy, in situ hybridization, and the polymerase chain reaction," *Obstet. Gynecol.*, 81(3):402-408, 1993.
Scheurlen et al., "Chronic autoimmune thrombopenia/neutropenia in a boy with persistent parvovirus B19 infection," *J. Clin. Virol.*, 20(3):173-178, 2001.
Servant et al., "Genetic diversity within human erythroviruses: identification of three genotypes," *J. Virol.*, 76(18):9124-9134, 2002.
Shields et al., "In vitro hematopoiesis is inhibited in humans and non-human primates by recombinant parvo virus capsid," *American Journal of Obstetrics & Gynecology*, 182(part 2):S15 (abstract 17), 2000.
Shneerson et al., "Febrile illness due to a parvovirus," *Br Med J.*, 280(6231):1580, 1980.
Söderlund et al., "Persistence of parvovirus B19 DNA in synovial membranes of young patients with and without chronic arthropathy," *Lancet*, 349(9058):1063-1065, 1997.
Török, "Unusual clinical manifestations reported in patients with parvovirus B19 infection," Anderson and Young (eds): Human Parvovirus B19, *Monogr. Virol.*, 20:61-92, 1997.
Tóvári et al., "Self limiting lupus-like symptoms in patients with parvovirus B19 infection," *Ann. Rheum. Dis.*, 61(7):662-663, 2002.
Trapani et al., "Human parvovirus B19 infection: its relationship with systemic lupus erythematosus," *Semin. Arthritis Rheum.*, 28(5):319-325, 1999.
Von Landenberg et al., "Antiphospholipid antibodies in pediatric and adult patients with rheumatic disease are associated with parvovirus B19 infection," *Arthritis Rheum.*, 48(7):1939-1947, 2003.
Vuorinen et al., "Presence of parvovirus B19 DNA in chronic urticaric and healthy human skin," *J. Clin. Virol.*, 25(2):217-221, 2002.
Wardeh and Marik, "Acute lung injury due to parvovirus pneumonia," *J. Internal Med.*, 244(3):257-260, 1998.
Yaegashi et al., "The incidence of, and factors leading to, parvovirus B19-related hydrops fetalis following maternal infection; report of 10 cases and meta-analysis," *J Infect.*, 37(1):28-35, 1998.
Yoto et al., "Human parvovirus B19 and meningoencephalitis," *Lancet*, 358(9299):2168, 2001.

* cited by examiner

Alignment of Parvovirus VP1 protein (3 different genotypes)

```
GENOTYP 1 (M13178)   MSKKSGKWWESDDKFAKAVYQQFVEFYEKVTGTDLELIQILKDHYNISLDNPLENPSSLF 60
GENOTYP 2 (AY064475) MSKKSDKWWESDDKFAKDVYKQFVEFYEKVTETDLELIQILKDHYNISLDNPLENPSSLF 60
GENOTYP 3 (AX003421) MSKTTNKWWESSDKFAQDVYKQFVQFYEKATGTDLELIQILKDHYNISLDNPLENPSSLF 60
                     ***ooo*****o****oo**o***o****o*o****************************

GENOTYP 1 (M13178)   DLVARIKNNLKNSPDLYSHHFQSHGQLSDHPHALSSSSSHAEPRGENAVLSSEDLHKPGQ 120
GENOTYP 2 (AY064475) DLVARIKSNLKDTPDLYSHHFQSHGQLFDHPHALSPSSSHTEPRGEDAVLSSEDLHKPGQ 120
GENOTYP 3 (AX003421) DLVARIKSNLKNSPDLYSHHFQSHGQLSDHPHALSSSNSSAEPRGENAVLSSEDLHKPGQ 120
                     *******o***oo**************o*******o*o*oo*****o*************

GENOTYP 1 (M13178)   VSVQLPGTNYVGPGNELQAGPPQSAVDSAARIHDFRYSQLAKLGINPYTHWTVADEELLK 180
GENOTYP 2 (AY064475) VSIQLPGTNYIGPGNELQAGPPQSAVDSAARIHDFRYSQLAKLGINPYTHWTVADEELLK 180
GENOTYP 3 (AX003421) VSIQLPGTNYVGPGNELQAGPPQNAVDSAARIHDFRYSQLAKLGINPYTHWTVADEELLK 180
                     **o*******o*************o***********************************

GENOTYP 1 (M13178)   NIKNETGFQAQVVKDYFTLKGAAAPVAHFQGSLPEVPAYNASEKYPSMTSVNSAEASTGA 240
GENOTYP 2 (AY064475) NIKNETGFQAQAVKDYFTLKGAAAPVAHFQGSLPEVPAYNASEKYPSMTSVNSAEASTGA 240
GENOTYP 3 (AX003421) NIKNETGFQAQAVKDYFTLKGAAAPVAHFQGSLPEVPAYNASEKYPSMTSVNSAEASTGA 240
                     ***********o************************************************

GENOTYP 1 (M13178)   GGGGSNSVKSMWSEGATFSANSVTCTFSRQFLIPYDPEHHYKVFSPAASSCHNASGKEAK 300
GENOTYP 2 (AY064475) GGGGSNPVKSMWSEGATFTANSVTCTFSRQFLIPYEPEHRYKVFSPAASSCHNASGKEAK 300
GENOTYP 3 (AX003421) GGGGSNPTKSMWSEGATFTANSVTCTFSRQFLIPYDPEHHYKVFSPAASSCHNASGKEAK 300
                     ******oo**********o****************o***o********************

GENOTYP 1 (M13178)   VCTISPIMGYSTPWRYLDFNALNLFFSPLEFQHLIENYGSIAPDALTVTISEIAVKDVTD 360
GENOTYP 2 (AY064475) VCTISPIMGYSTPWRYLDFNALNLFFSPLEFQHLIENYGSIAPDALTVTISEIAVKDVTD 360
GENOTYP 3 (AX003421) VCTISPIMGYSTPWRYLDFNALNLFFSPLEFQHLIENYGSIAPDALTVTISEIAVKDVTD 360
                     ************************************************************

GENOTYP 1 (M13178)   KTGGGVQVTDSTTGRLCMLVDHEYKYPYVLGQGQDTLAPELPIWVYFPPQYAYLTVGDVN 420
GENOTYP 2 (AY064475) KTGGGVQVTDSTTGRLCMLVDHEYKYPYVLGQGQDTLAPELPIWVYFPPQYAYLTAGDVN 420
GENOTYP 3 (AX003421) KTGGGVQVTDSTTGRLCMLVDHEYKYPYVLGQGQDTLAPELPIWVYFPPQYAYLTVGEVN 420
                     *******************************************************o*o**
```

Fig.2

```
GENOTYP 1 (M13178)    TQGISGDSKKLASEESAFYVLEHSSFQLLGTGGTASMSYKFPPVPPENLEGCSQHFYEMY 480
GENOTYP 2 (AY064475)  TQGISGDSKKLASEESAFYVLEHSSFELLGTGGSATMSYKFPPVPPENLEGCSQHFYEMY 480
GENOTYP 3 (AX003421)  TQGISGDSKKLASEESAFYVLEHSSFELLGTGGSATMSYKFPAVPPENLEGCSQHFYEMY 480
                      **************************o******o*o******o*****************

GENOTYP 1 (M13178)    NPLYGSRLGVPDTLGGDPKFRSLTHEDHAIQPQNFMPGPLVNSVSTKEGDSSNTGAGKAL 540
GENOTYP 2 (AY064475)  NPLYGSRLGVPDTLGGDPKFRSLTHEDHAIQPQNFMPGPLVNSVSTKEGDISNTGAGKAL 540
GENOTYP 3 (AX003421)  NPLYGSRLGVPDTLGGDPKFRSLTHEDHAIQPQNFMPGPLINSVSTKEGDNSNTGAGKAL 540
                      ****************************************o*********o*********

GENOTYP 1 (M13178)    TGLSTGTSQNTRISLRPGPVSQPYHHWDTDKYVTGINAISHGQTTYGNAEDKEYQQGVGR 600
GENOTYP 2 (AY064475)  TGLSTGTSQSTRISLRPGPVSQPYHHWDTDKYVTGINAISHGQTTYGNAEDKEYQQGVGR 600
GENOTYP 3 (AX003421)  TGLSTGTSQNTRISLRPGPVSQPYHHWDTDKYVTGINAISHGQTTYGNAEDKEYQQGVGR 600
                      *********o**************************************************

GENOTYP 1 (M13178)    FPNEKEQLKQLQGLNMHTYFPNKGTQQYTDQIERPLMVGSVWNRRALHYESQLWSKIPNL 660
GENOTYP 2 (AY064475)  FPNEKEQLKQLQGLNIHTYFPNKGTQQYTDQIERPLMVGSVWNRRALHYESQLWSKIPNL 660
GENOTYP 3 (AX003421)  FPNEKEQLKQLQGLNMHTYFPNKGTQQYTDQIERPLMVGSVWNRRALHYESQLWSKIPNL 660
                      ***************o********************************************

GENOTYP 1 (M13178)    DDSFKTQFAALGGWGLHQPPPQIFLKILPQSGPIGGIKSMGITTLVQYAVGIMTVTMTFK 720
GENOTYP 2 (AY064475)  DDSFKTQFAALGGWGLHQPPPQIFLKILPQSGPIGGIKSMGITTLVQYAVGIMTVTMTFK 720
GENOTYP 3 (AX003421)  DDSFKTQFAALGGWGLHQPPPQIFLKILPQSGPIGGIKSMGITTLVQYAVGIMTVTMTFK 720
                      ************************************************************

GENOTYP 1 (M13178)    LGPRKATGRWNPQPGVYPPHAAGHLPYVLYDPTATDAKQHHRHGYEKPEELWTAKSRVHP 780
GENOTYP 2 (AY064475)  LGPRKATGRWNPQPGVYPPHAAGHLPYVLYDPTATDAKQHHRHGYEKPEELWTAKSRVHP 780
GENOTYP 3 (AX003421)  LGPRKATGRWNPQPGVYPPHAAGHLPYVLYDPTATDAKQHHRHGYEKPEELWTAKSRVHP 780
                      ************************************************************

GENOTYP 1 (M13178)    L 781
GENOTYP 2 (AY064475)  L 781
GENOTYP 3 (AX003421)  L 781
                      *
```

conserved amino acids in all 3 genotypes: 743/781 (95%)

alignment performed by CLUSTAL W (1.8) multiple sequence alignment

Fig. 2 (Continued)

MODIFIED VP1-CAPSID PROTEIN OF PARVOVIRUS B19

This application is a national phase application under 35 U.S.C. §371 of International Application No. PCT/EP2005/054771 filed 23 Sep. 2005, which claims priority to European Patent Application No. 04450180.7 filed 24 Sep. 2004. The entire text of each of the above-referenced disclosures is specifically incorporated herein by reference without disclaimer.

The present invention relates to modified Parvovirus B19 capsid proteins and particles, their uses and the preparation of medicaments including vaccines for the treatment of parvovirus B19 associated diseases.

Parvovirus B19 was discovered in 1975 as cause of systemic infections of adults who either were asymptomatic or had mild non specific symptoms such as headache, pyrexia, malaise, fatigue, and myalgia (1, 2, 3). In 1984 parvovirus B19 was identified as the etiological agent of erythema infectiosum, also known as fifth disease (4). The virus is spread worldwide but restricted exclusively to human hosts. With respect to regional differences about 40 to 60 percent of the population displays antibodies against viral proteins at an age of 20 years. The infection is endemic, however reaches regional outbreaks during late winter and spring time. The virus is very stable. In general it is transmitted orally from individuals with acute infection (5). Beside this major route of infection the virus may be transmitted through parenterally administered blood and blood derived products and vertically from mother to fetus (6, 7, 8, 9). Massive productive replication of parvovirus B19 takes place in erythroid progenitor cells (10). Therefore during acute infection the virus load is extremely high and up to $10^{13}$ particles and/or virus genomes may be present per milliliter of the peripheral blood. The virus binds to erythrocyte precursor cells using the blood group antigen P (globoside) as the cellular receptor for adsorption (11). After the infection and elimination from the peripheral blood viral genomes have been shown to be present in cells of bone marrow and skin, in synovial cells, in tissues from liver and in the endothelium of the myocard (12, 13, 14, 15, 16, 17). At present it is not clear if these cells produce viral proteins and/or infectious B19 particles and if the virus genome can be reactivated to productive replication.

In common parvovirus B19 infection is without clinical symptoms or may result in a flu like disease. Particularly children may suffer from erythema infectiosum (fifth disease), a self limiting rash illness (18, 19, 20). Parvovirus B19 has been further associated with a wide spectrum of diseases (Table 1): Transient anemia, leucocytopenia or thrombocytopenia may occur without requiring any therapy. However, in some patients severe thrombocytopenia, pure red cell aplasia or pancytopenia were observed. Besides these hematologic sequelae of acute infection hepatitis, myocarditis, myositis, acute lung injury and neurological disease may occur occasionally (12, 21, 22, 23, 24). In pregnant women spontaneous abortion, non-immune hydrops fetalis and intrauterine fetal death have been reported as clinical manifestations (25, 26). In non immune pregnant women with acute infection a fetal death rate of about 9% has been found (9, 27). However there are also studies which describe a higher percentage for the development of hydrops fetalis in B19-infected, non-immune pregnant women (28). Depending on the hematologic status of the host; e.g. patients with sickle cell anemia or thalassemia, B19 infection results in aplastic crisis. Persistent parvovirus B19 infection has been reported in patients both with and without underlying immunodeficiencies (29, 30).

Beside these general manifestations parvovirus B19 infection may induce a broad spectrum of autoimmune phenomena. Autoimmune cytopenias are well known hematological disorders that may affect any bone-marrow cell lineage. In the mass majority of cases only one of the cell lines is affected. However, concurrent autoimmune-mediated destruction of neutrophil granulocytes and thrombocytes due to persistent parvovirus B19 infection is known (31). Parvovirus B19 has been identified as a possible trigger in some cases of immune thrombocytopenia (32, 33, 34, 35). The clinical spectrum of autoimmune joint disease ranges from mild arthralgias to severe necrotizing vasculitis (Table 1). In some outbreaks of erythema infectiosum, arthralgias and arthritis have been commonly reported. B19-infection may produce a symmetrical peripheral polyarthropathy in adults. Symptoms are usually self-limited but may persist for several months. Occasionally viremia combined with IgM/IgG-antibodies against structural proteins VP1 and/or VP2 has been shown in patients with long lasting polyarthralgia/polyarthritis. Some of them met the criteria of rheumatoid arthritis (RA) (26, 37). However development of RA after acute parvovirus infection seems to be rare (38, 39). In children the relation of the B19-infection with arthritis-arthralgias is well known. Some of the affected children may develop chronic arthritis indistinguishable from juvenile idiopathic arthritis (40, 41, 42, 43). The clinical spectrum encompasses mono-, oligo- and polyarthritis. Furthermore persisting viremia is frequently observed in children with systemic juvenile idiopathic arthritis. In children with various forms of juvenile arthritis B19-DNA was amplified in 57% of serum and/or synovial fluid from those with previous parvovirus B19 infection. In many patients the continuous presence of viral particles and immunocomplexes could be demonstrated in the peripheral blood as well as in synovial fluid (44). Despite the development and presence of B19-specific immunoreaction the children were incapable of eliminating the virus and showed a prolonged state of viremia or viral persistence in synovial fluid.

Parvovirus B19 infection has been associated with various forms of vasculitis, collagenosis and may mimic systemic lupus erythematosus (SLE) in children and adults (39, 45, 46). Similar to the situation in arthritis patients also in SLE-patients parvovirus B19 infection has been described both as the agent causing or triggering the rheumatic disease (47, 48, 49, 50, 51). Recently, an association between persistent parvovirus B19 infection and the production of anti-phospholipid antibodies in pediatric and adult patients with rheumatic disease was described (52). The antiphospholipid syndrome (APS) (53) is, like some parvovirus B19 infections, characterized by a wide variety of hemocytopenic and vaso-occlusive manifestations. Additionally recurrent fetal loss and the association with autoantibodies directed against negatively charged phospholipids and protein cofactors, mainly β2-glycoprotein-I are important features of the APS. The hypothesis regarding a common pathogenicity of the anti-phospholipid syndrome and the autoimmunity features observed in B19-infection is supported not only by the close association between the presence of anti-phospholipid antibodies and parvovirus B19 infection but also by the similarity in the presenting of clinical symptoms in patients with parvovirus B19 infection and patients with the APS.

The icosahedral capsid of parvovirus B19 consist of two structural proteins, VP1 (83 kDa) and VP2 (58 kDa), which are identical except for 227 amino acids (aa) at the amino-terminal end of the VP1 protein (the VP1 unique region). A phospholipase A2 motif is present in the amino acid sequence of the VP1 unique region spanning positions 130 to 195 (Phospholipase A2 active center) (54). One of the pathogenic mechanisms involved in triggering the production of anti-phospholipid antibodies might be the phospholipase-A2-like activity observed in the VP1-unique region of the structural protein VP1 of parvovirus B19 (54). This enzyme activity is present in infectious B19-particles, in recombinant empty capsids consisting of VP1/VP2-proteins and in preparations of purified VP1-unique region. It may contribute to the inflammatory processes induced by the production of leukotrienes and prostaglandines, but may also lead to the generation of unusual natural cleavage products from cellular phospholipid compounds that may induce aPL-antibodies in combination with a distinct genetic background.

Until now a vaccine to prevent parvovirus B19 infection is not available. With respect to the severe courses that are observed in association with the infection, the problems associated with the infection in pregnant women and the virus' potential to induce a wide variety of autoimmune diseases the development of a safe vaccine protecting parvovirus B19 infections Purified recombinant empty capsids consisting of VP1/VP2-proteins expressed by baculovirus vectors have been used in a phase I trial and showed the successful induction of B19-neutralizing antibodies in volunteers (55). The application of this vaccine was, however combined with a variety of side effects. Besides swelling at the injections side, more general signs of ill feeling as fever, head ache and diarrhoe were reported by more than 50 percent of the volunteers. These side effects indicate that the application of the vaccine results in systemic manifestation of side effects that are known to be associated with the activation of basic defence reactions associated with inflammation. During early immune reactions following e.g. infections these effects are mainly associated with the activation of cellular and cytosolic phospholipases A2. These enzymes are responsible for the production of arachodonic acid as precursor for prostaglandin and leukotriene production, the induction of various cyto- and chemokines leading to fever and general ill feeling. The side effects observed by Ballou and coworkers using VP1/VP2 empty capsids produced by recombinant baculovirus (55) is likely due to the phospholipase-A2-like activity which is part of the VP1-unique region of the viral capsid protein VP1.

The problem underlining the present inventions is to provide medicaments such as a parvovirus B19 vaccine for the prevention and/or treatment of parvovirus B19 associated diseases with minimal side effects.

This problem is addressed by the present invention through advantageously alternating/modifying the VP1-capsid protein of parvovirus B19 thus reducing the phospholipase-A2-like activity of the VP1-unique region of the viral capsid protein VP1.

According to one aspect of the present invention, there is provided a modified VP1-capsid protein of parvovirus B19 having a reduced phospholipase A2-like enzyme activity as compared to the wild type VP1-capsid protein of parvovirus B19 having the amino acid sequence of Seq. ID No 1.

According to the present invention, the natural phospholipase activity is reduced (which includes complete abolition of the activity). Therefore, regions of the protein which are involved in reduction of this phospholipase activity can be altered according to the present invention. These changes compared to wild type sequence may be introduced by amino acid exchanges, deletions or insertions. Reduction of phospholipase activity can easily be assessed by the skilled man in the art e.g. by relying on the methodology disclosed herein, especially according to the test described in FIG. 2 of Dorsch et al, 2002 (54). On the other hand, the changes should not significantly alter the immunological performance of the vaccine (i.e. in that the immunogenic properties should not be adversely affected by the mutation).

According to a preferred embodiment of the present invention, the amino acid residues in the VP1-unique region of the VP1-capsid protein (amino acids 100-220, specifically 130 to 195) are altered. This region is highly conserved in all three genotypes of parvovirus B19 that have been identified until today (60; FIG. 2). However, although obviously this region is conserved, differences in the activity of different parvovirus B19 genotypes can be observed: Genotype 1: 100%, Genotype 2: 70%, genotype 3: 59%. Reference to wild type activity means that the closest genotype is selected for comparison of wild type mutant (e.g. if a mutant of genotype 2 is made, phospholipase activity of the mutant is compared to wild type of genotype 2).

In general, whole VP1 protein may be subject to the introduction of mutations for reducing or eliminating phospholipase A2-like activity of this protein. However, since mutations outside the VP1 unique region (amino acids 100-220, specifically 130 to 195) have usually a low, if any, reduction potential on the phospholipase activity, mutations inside this VP1 unique region are preferred according to the present invention. Nevertheless, also in the region outside the VP1 unique region mutations according to the present invention may be introduced, e.g. by amino truncation or by mutations in the region of amino acid 50-90, especially 59-81. Whether a mutation fulfills the expected reduction of phospholipase activity can easily be addressed by the combination of the expression of the mutant with a functional activity assay. Such phospholipase activity tests are well available in the art and also described herein.

Specifically preferred sites of mutation are around the $Ca^{2+}$ binding amino acids (Tyr(130), Gly(132), Gly(134), Asp(154)) or around the catalytic network (His(153), Tyr (157), Tyr(168)), including the phospholipid binding (Lys (162)), i.e. amino acids 125-140 and 150-175, especially 127-137, 152-160 and 165 to 171 (see also SeqID No. 1 and FIG. 2 for sequences).

Preferred exchanges are the exchanges usually used in enzyme activity reducing mutation strategies, e.g. replacing an amino acid with a functional side chain (His, Lys, Tyr, Asp, Glu, Ser, Thr, Asn, Gln, etc.) with an amino acid with a non functional side chain of the same or different size (Ala, Phe, Leu, Pro, Ile, etc.) or with a different functional side chain (e.g. Asn→Asp, Gln→Ser, etc.). Sometimes, also a slight difference is sufficient (Val→Ala, Ser→Thr, etc.).

According to another preferred embodiment of the present invention, the altered amino acid residues reside in the phospholipase A2 center of the VP1-unique region of the VP1-capsid protein.

According to a further preferred embodiment of the present invention, one or more of the conserved amino acid residues in the active centre of the phospholipase A2 are altered.

Amino acid residues at position 153: histidine; 157: tyrosine; 162: lysine; 168: tyrosine; 195: aspartic acid have been described as parts of the catalytic triad of bovine pancreatic phospholipase A2 and to be involved in substrate orientation and specificity (58, 59). Modification of one or more of the residues of 153: histidine, 157: tyrosine, 162: lysine, 168: tyrosine result in an even more pronounced reduction of phospholipase A2-like activity, whereas modifying and alternating the residue of 195: aspartic acid result in an enhanced phospholipase A2-like activity.

Thus according to another preferred embodiment of the present invention, one or more of the amino acid residues are altered at position 153: histidine; position 157: tyrosine; position 162: lysine; and/or position 168: tyrosine.

According to yet another preferred embodiment, histidine 153 is altered into alanine; tyrosine 157 is altered into phenylalanine; lysine 162 is altered into leucine and/or tyrosine 168 is altered into phenylalanine.

In general, the mutation according to the present invention should be as minimal as possible (in order not to alter immunogenic properties too much): usually a low number of amino acid substitutions (6, 5, 4, 3, 2 or, preferably, 1) and a short insertion or deletion (30, 20, 10, 5 or 1 amino acids) should be sufficient to efficiently reduce or remove phospholipase activity. However longer insertions, deletion (50, 100, 200 amino acids) or a higher number of substitutions are not excluded, as long as the immunogenic properties are not significantly changed. However, the latter, multiple mutations are also less preferred due to cost aspects.

Whether the mutants have similar immunogenic properties or not can easily be determined e.g. by reacting with specific antibodies or by determining in vitro or in vivo ability to induce immune responses. Generally, the mutants should exhibit (with or without specific adjuvants) about 50% of in vivo immunogenicity as the wild type (without adjuvants, or preferably, with the same adjuvant as the mutant), determined by at least one scientifically applied and (by peer review) accepted method, e.g. antibody binding, ELISpot assays, etc. (see also: example section of the present application).

According to the present invention, the modified VP1-unique region or the modified VP1-capsid protein of the present invention results in a reduced phospholipase A2-like enzyme activity as compared to the wild type VP1-capsid protein. Preferably, the reduction is at least 30% compared to the wild type (i.e. 70% or less of wild type activity). Further preferred is a reduction to 50% or less, 30% or less, 20% or less, or 10% or less of the wild type activity. Reference activity of wild type and mutant are preferably determined according to a standardized phospholipase A2-like enzyme activity test, especially according to FIG. 2 of (54).

Especially, those mutants which completely lack this activity (i.e. below 5%, below 1% or below 0.1%, depending on the detection limits of the method) are most suitable for vaccine use and safety according to the present invention.

Preferably, the alternation of the amino acid residues is made by site-directed mutagenesis.

According to another aspect of the present invention, there is provided an isolated nucleic acid molecule encoding the modified VP1-capsid protein provided by the present invention.

According to a further aspect of the present invention, there is provided a recombinant expression vector comprising the nucleic acid molecules encoding the modified VP1-unique region and the modified VP1-capsid protein provided by the present invention.

Preferably, the recombinant expression vector according to the present invention further comprises VP2-capsid protein of parvovirus B19 especially wherein the protein is being expressable together with the modified VP-1 capsid. However, also the combined expression of the VP1 and VP2 proteins using two vectors that are introduced into the cells has its advantages for specific purposes.

More preferably, the recombinant expression vector according to the present invention comprises a fusion product in that the modified VP1-unique region or the modified VP1-capsid protein is fused to the VP2-capsid protein.

According to another aspect of the present invention, there is provided a host cell comprising the recombinant expression vector according to the present invention.

Preferably, the host cell is *E. coli*, yeast, or an animal cell.

Most preferably the host cell is *Saccharomyces cerevisiae*. This species of yeast has been used for two decades to produce recombinant HBsAg-particles that protect against hepatitis B virus infection. The use of recombinant *S. cerevisiae* derived HBV vaccines has been shown to be safe, side effects are observed only very rarely.

According to another aspect of the present invention, there is provided a process of producing the modified VP1-unique region or the modified VP1-capsid protein or the fusion product of the modified VP1-capsid protein and VP2-capsid protein by transforming a host cell, expressing the VP1-capsid (and optionally the VP2-capsid), recovering the protein(s), optionally as virus-like particles, using the host cell according to the present invention.

Preferably in such process the modified VP1-unique region and/or the modified VP1-capsid protein and/or the fusion product of the modified VP1-capsid protein and VP2-capsid protein are isolated and/or purified.

According to another aspect of the present invention, there is provided the modified VP1-unique region, and/or the modified VP1-capsid protein or the fusion product of the modified VP1-unique region and VP2-capsid protein obtainable by the process according to the present invention.

According to yet another aspect of the present invention, there is provided the modified VP1-unique region and/or the modified VP1-protein or the fusion product of the modified VP1-unique region and/or the modified VP1-protein and VP2-capsid protein for use as medicaments.

According to a further aspect of the present invention, there is provided the use of the modified VP1-unique region, the modified VP1-protein with or without VP2-capsid protein for the manufacture of a medicament for the treatment against parvovirus B19 infection and/or parvovirus B19 associated autoimmune and rheumatic diseases.

According to still a further aspect of the present invention, there is provided the use of the fusion product of the modified VP1-unique region, the modified VP1-protein and VP2 capsid protein for the manufacture of a medicament for the treatment against parvovirus B19 infection and/or parvovirus B19 associated autoimmune and rheumatic diseases.

Preferably the treatment is against Arthralgias; Arthritis; more preferably Monoarthritis, Oligoarthritis, Polyarthritis, Rheumatoid arthritis and/or Juvenile idiopathic arthritis; Systemic lupus erythematosus (SLE); Vasculitis, more preferably Leukoclastic vasculitis, Purpura Henlein-Schoenoch, Papular-purpuric gloves-and-socks syndrome (PPGSS), Kawasaki disease, Giant cell arteritis (GCA), Polyarteritis nodosa and/or Wegener's granulomatosis; Dermatomyositis; Autoimmune neutropenia; Autoimmune thrombocytpenia; Idiopathic thrombocytopenic purpura (ITP); Autoimmune hemolytic anemia; and/or Virus-associated hemophagocytic syndrome (VAHS).

According to another aspect of the present invention, there is provided the use of the modified VP1-unique region, the modified VP1 capsid protein or the fusion product of the modified VP1-unique region and VP2-capsid protein according to the present invention in an assay for detecting antibodies directed against the B19 virus protein VP1 in a sample to be tested.

According to a further aspect of the present invention, there is provided the use of the host cells of the present invention in an assay for detecting antibodies directed against the B19 virus protein VP1 in a sample to be tested.

According to another aspect of the present invention, there is provided the recombinant virus-like particles consisting of the modified VP1-capsid protein according to the present invention with or without VP2-capsid protein.

According to yet another aspect of the present invention, there is provided the recombinant virus-like particles consisting of the fusion product of the modified VP1-unique region, the modified VP1-capsid protein and VP2-capsid protein according to the present invention.

According to another aspect of the present invention, those recombinant virus-like particles can be used for the manufacture of a medicament for the treatment against parvovirus B19 infection and/or parvovirus B19 associated autoimmune and rheumatic diseases.

The treatment is preferably against Arthralgias; Arthritis; more preferably Monoarthritis, Oligoarthritis, Polyarthritis, Rheumatoid arthritis and/or Juvenile idiopathic arthritis; Systemic lupus erythematosus (SLE); Vasculitis, more preferably Leukoclastic vasculitis, Purpura Henlein-Schoenoch, Papular-purpuric gloves-and-socks syndrome (PPGSS), Kawasaki disease, Giant cell arteritis (GCA), Polyarteritis nodosa and/or Wegener's granulomatosis; Dermatomyositis; Autoimmune neutropenia; Autoimmune thrombocytpenia; Idiopathic thrombocytopenic purpura (ITP); Autoimmune hemolytic anemia; and/or Virus-associated hemophagocytic syndrome (VAHS).

According to another aspect of the present invention, there is provided the use of the recombinant virus-like particles according to the present invention in an assay for detecting antibodies directed against the B19 virus protein VP1 in a sample to be tested.

According to a further aspect of the present invention, there is provided a pharmaceutical composition, especially a vaccine preparation for inducing an immune response which provides protection against the human parvovirus B19, comprising the modified VP1-unique region, the modified VP1-capsid protein according to the present invention, with or without the VP2-capsid protein.

According to another aspect of the present invention, there is provided a pharmaceutical composition, especially a vaccine preparation for inducing an immune response which provides protection against the human parvovirus B19, comprising the fusion product of the modified VP1-capsid protein according to the present invention.

According to still another aspect of the present invention, there is provided a pharmaceutical composition, especially a vaccine preparation for inducing an immune response which provides protection against the human parvovirus B19, comprising the recombinant virus-like particles according to the present invention.

Preferably, the pharmaceutical compositions according to the present invention are further comprising one or more carriers and/or adjuvants suitable for vaccination purposes.

Therefore, the compositions provided by the present invention, especially in the form of a vaccine, may further comprise an immunostimulatory substance, preferably selected from the group comprising a polycationic compound, preferably a polycationic polymer, more preferably a polycationic peptide, especially polyarginine, polylysine or an antimicrobial peptide.polymers; immunostimulatory deoxynucleotides (ODNs); peptides containing at least two LysLeuLys motifs; neuroactive compounds, especially human growth hormone; alumn, Freund's complete or incomplete adjuvants or combinations thereof.

The present vaccine preferably comprises an modified VP1 capsid protein according to the present invention as antigen a peptide comprising a sequence $R_1$—XZXZ$_N$XZX—$R_2$, (SEQ ID NOs: 5-9, wherein: xzxzzzxzx=SEQ ID NO: 5; xzxzzzzxzx=SEQ ID NO: 6; xzxzzzzzxzx=SEQ ID NO: 7; xzxzzzzzzxzx=SEQ ID NO: 8; xzxzzzzzzzxzx=SEQ ID NO: 9) whereby N is a whole number between 3 and 7, preferably 5, X is a positively charged natural and/or non-natural amino acid residue, Z is an amino acid residue selected from the group consisting of L, V, I, F and/or W, and $R_1$ and $R_2$ are selected independently one from the other from the group consisting of —H, —$NH_2$, —$COCH_3$, —COH, a peptide with up to 20 amino acid residues or a peptide reactive group or a peptide linker with or without a peptide; X—$R_2$ may be an amide, ester or thioester of the C-terminal amino acid residue of the peptide (in the following also referred to as "Peptide A") and/or an immunostimulatory oligodeoxynucleic acid molecule (ODN) having the structure according to the formula (I)

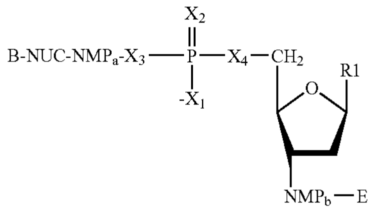

wherein

R1 is selected from hypoxanthine and uracile, any X is O or S, any NMP is a 2' deoxynucleoside monophosphate or monothiophosphate, selected from the group consisting of deoxyadenosine-, deoxyguanosine-, deoxyinosine-, deoxycytosine-, deoxyuridine-, deoxythymidine-, 2-methyl-deoxyinosine-, 5-methyl-deoxycytosine, deoxypseudouridine-, deoxyribosepurine-, 2-aminodeoxyribosepurine-, 6-S-deoxyguanine-, 2-dimethyldeoxyguanosine- or N-isopentenyl-deoxyadenosine-monophosphate or -monothiophosphate, NUC is a 2' deoxynucleoside, selected from the group consisting of deoxyadenosine-, deoxyguanosine-, deoxyinosine-, deoxycytosine-, deoxyinosine-, deoxythymidine-, 2-methyl-deoxyuridine-, 5-methyl-deoxycytosine-, deoxypseudouridine-, deoxyribosepurine-2-amino-deoxyribosepurine-, 6-S-deoxyguanine-, 2-dimethyldeoxyguanosine-, or N-isopentenyl-deoxyadenosine, a and b are integers from 0 to 100 with the proviso that a+b is between 4 and 150, and B and E are common groups for 5' or 3' ends of nucleic acid molecules (in the following also referred to as "I-/U-ODN").

Of course, the present vaccine may further contain other substances, e.g. suitable pharmaceutically acceptable diluents or carrier, buffer or stabilising substances, etc.

The vaccine according to the present invention may also contain other or additional adjuvants, especially an $Al(OH)_3$ adjuvant (Alum).

Alum, as meant herein includes all forms of $Al^{3+}$ based adjuvants used in human and animal medicine and research. Especially, it includes all forms of aluminum hydroxide as defined in Römpp, 10th Ed. pages 139/140, gel forms thereof, aluminum phosphate, etc.

The polycationic peptides or compound to be used according to the present invention may be any polycationic compound which shows the characteristic effect according to the WO 97/30721. Preferred polycationic compounds are selected from basic polypeptides, organic polycations, basic polyaminoacids or mixtures thereof. These polyaminoacids should have a chain length of at least 4 amino acid residues. Especially preferred are substances containing peptidic bounds, like polylysine, polyarginine and polypeptides containing more than 20%, especially more than 50% of basic amino acids in a range of more than 8, especially more than 20, amino acid residues or mixtures thereof. Other preferred polycations and their pharmaceutical compositions are described in WO 97/30721 (e.g. polyethyleneimine) and WO 99/38528. Preferably these polypeptides contain between 20 and 500 amino acid residues, especially between 30 and 200 residues.

These polycationic compounds may be produced chemically or recombinantly or may be derived from natural sources.

Cationic (poly)peptides may also be polycationic antibacterial microbial peptides. These (poly)peptides may be of prokaryotic or eukaryotic origin or may be produced chemically or recombinantly. Peptides may also belong to the class naturally occurring antimicrobial peptides. Such host defense peptides or defensives are also a preferred form of the polycationic polymer according to the present invention. Generally, a compound allowing as an end product activation (or down-regulation) of the adaptive immune system, preferably mediated by APCs (including dendritic cells) is used as polycationic polymer.

Furthermore, also neuroactive compounds, such as (human) growth hormone (as described e.g. in WO01/24822) may be used as immunostimulants (Immunizers).

Polycationic compounds derived from natural sources include HIV-REV or HIV-TAT (derived cationic peptides, antennapedia peptides, chitosan or other derivatives of chitin) or other peptides derived from these peptides or proteins by biochemical or recombinant production. Other preferred polycationic compounds are cathelin or related or derived substances from cathelicidin, especially mouse, bovine or especially human cathelicidins and/or cathelicidins. Related or derived cathelicidin substances contain the whole or parts of the cathelicidin sequence with at least 15-20 amino acid residues. Derivations may include the substitution or modification of the natural amino acids by amino acids which are not among the 20 standard amino acids. Moreover, further cationic residues may be introduced into such cathelicidin molecules. These cathelicidin molecules are preferred to be combined with the antigen/vaccine composition according to the present invention. However, these cathelin molecules surprisingly have turned out to be also effective as an adjuvant for a antigen without the addition of further adjuvants. It is therefore possible to use such cathelicidin molecules as efficient adjuvants in vaccine formulations with or without further immunactivating substances.

The vaccine according to the present invention preferably contains as Peptide A $KLKL_5KLK$ (SEQ ID NO: 4) and/or as I-/U-ODN oligo $d(IC)_{13}$ (The combination of Peptide A and Oligo-$d(IC)_{13}$ is also referred as IC31). These two substances are specifically advantageous according to the present invention.

The vaccine according to the present invention may contain an oligodeoxynucleotide containing a CpG-motif as immunomodulating nucleic acids. The immunomodulating nucleic acids to be used according to the present invention can be of synthetic, prokaryotic and eukaryotic origin. In the case of eukaryotic origin, DNA should be derived from, based on the phylogenetic tree, less developed species (e.g. insects, but also others). In a preferred embodiment of the invention the immunogenic oligodeoxynucleotide (ODN) is a synthetically produced DNA-molecule or mixtures of such molecules. Derivates or modifications of ODNs such as thiophosphate substituted analogues (thiophosphate residues substitute for phosphate) as for example described in U.S. Pat. No. 5,723,335 and U.S. Pat. No. 5,663,153, and other derivatives and modifications, which preferably stabilize the immunostimulatory composition(s) but do not change their immunological properties, are also included. A preferred sequence motif is a six base DNA motif containing an (unmethylated) CpG dinucleotide flanked by two 5' purines and two 3' pyrimidines (5'-Pur-Pur-C-G-Pyr-Pyr-3'). The CpG motifs contained in the ODNs according to the present invention are more common in microbial than higher vertebrate DNA and display differences in the pattern of methylation. Surprisingly, sequences stimulating mouse APCs are not very efficient for human cells. Preferred palindromic or non-palindromic ODNs to be used according to the present invention are disclosed e.g. in Austrian Patent applications A 1973/2000, A 805/2001, EP 0 468 520 A2, WO 96/02555, WO 98/16247, WO 98/18810, WO 98/37919, WO 98/40100, WO 98/52581, WO 98/52962, WO 99/51259 and WO 99/56755 all incorporated herein by reference. ODNs/DNAs may be produced chemically or recombinantly or may be derived from natural sources. Preferred natural sources are insects.

The vaccine according to the present invention may preferably contain a polycationic peptide and an oligodeoxynucleotide containing a CpG-motif in combination. The combination of CPG-ODN and polycationic peptide has improvement effects in vaccine compositions, which are comparable to the effects of the combination of Peptide A and I-/U-ODNs and cannot only be combined with Peptide A and I-/U-ODNs but even be used instead of them. Of course, also mixtures of different immunostimulatory nucleic acids (I-/U-ODNs, CpG-ODNs, . . . ) and Peptide A variants (as well as other Immunizers) may be used according to the present invention.

It has been shown previously (WO 02/13857) that naturally occurring, cathelicidin-derived antimicrobial peptides or derivatives thereof have an immune response stimulating activity and therefore constitute highly effective type 1 inducing adjuvants (Immunizers). Main sources of antimicrobial peptides are granules of neutrophils and epithelial cells lining the respiratory, gastro-intestinal and genitourinary tracts. In general they are found at those anatomical sites most exposed to microbial invasion, are secreted into internal body fluids or stored in cytoplasmic granules of professional phagocytes (neutrophils).

In the WO 02/32451 a type 1 inducing adjuvant (Immunizer) that is able to strongly enhance the immune response to a specific co-administered antigen and therefore constitutes a highly effective adjuvant is disclosed, Peptide A comprising a sequence $R_1$—$XZXZ_NXZX$—$R_2$ (SEQ ID NOs: 5-9). A specifically preferred peptide is KLKLLLLLKLK (SEQ ID NO: 4). Besides naturally occurring antimicrobial peptides, synthetic antimicrobial peptides have been produced and investigated. The synthetic antimicrobial peptide KLKLLLLLKLK-NH2 (SEQ ID NO: 4) was shown to have significant chemotherapeutic activity in *Staphylococcus aureus*-infected mice; human neutrophils were activated to produce the superoxide anion ($O2^-$) via cell surface calreticulin. The exact number and position of K and L was found to be critical for the antimicrobial activity of the synthetic peptide.

The present invention is especially beneficial if the vaccine is administered subcutaneously, intramusculary, intradermally or transdermally. However, other application forms, such as parenteral, intravenously, intranasally, oral or topical application, are also suitable for the present invention.

The Parvovirus antigen according to the present invention may be mixed with an adjuvant (Immunizer) (composition) or otherwise specifically formulated e.g. as liposome, retard formulation, etc.

The vaccines according to the present invention may be administered to an individual in effective amounts known to the skilled man in the art. Optimisation of antigen amount and Immunizer amount can be started from established amounts and using available methods.

According to another aspect of the present invention, there is provided a diagnostic kit comprising a modified VP1-unique region, a modified VP1-capsid protein according to the present invention and ancillary reagents.

According to still another aspect of the present invention, there is provided a diagnostic kit comprising a fusion product of the modified VP1-capsid protein according to the present invention and ancillary reagents.

According to a further aspect of the present invention, there is provided a diagnostic kit comprising a recombinant virus-like particles according to the present invention and ancillary reagents.

According to another aspect of the present invention, there is provided the use of the modified VP1-unique region, the modified VP1-capsid protein according to the present invention with or without VP2-capsid protein as an agent to modify the activity of host phospholipase A2 activity, e.g. by gene therapy on using antisense KNA or RNAi.

According to another aspect of the present invention, there is provided the use of the fusion product of the modified VP1-capsid protein according to the present invention as an agent to modify the activity of host phospholipase A2 activity.

According to a further aspect of the present invention, there is provided the use of the recombinant virus-like particles according to the present invention as an agent to modify the activity of host phospholipase A2 activity.

The present invention is further illustrated by the following examples and the figures, from which further features, embodiments and advantages may be taken. It is to be understood that the present examples are given by way of illustration only and not by way of limitation of the disclosure.

FIG. 1 shows an immunological comparison of wt and mutant protein

FIG. 2 shows an alignment of Parvovirus VP1 protein. GENOTYP 1=SEQ ID NO: 1; GENOTYP 2=SEQ ID NO: 2; GENOTYP 3=SEQ ID NO: 3.

Example 1

The production of VP1/VP2 antigens without enzymatic activity can be achieved by alteration of the residues that are part of the active centre by site-directed mutagenesis. Despite the fact that the overall size of cellular enzymes with $Ca^{2+}$-dependent phospholipase A2 activity and the viral VP1-unique region are different, alignments comparing the amino acid sequences revealed a number of conserved residues in the region that represents the active centre of the enzyme. Conserved amino acids were observed at the following positions:

Residue 153: histidine; residue 157: tyrosine; residue 162: lysine; residue 168: tyrosine; residue 195: aspartic acid. The respective amino acids have been described as parts of the catalytic triad of bovine pancreatic phospholipase A2 and to be involved in substrate orientation and specificity. Therefore the alteration of these residues in the VP1-unique region by site-directed mutagenesis was performed using polymerase chain reaction with mutated primer and overlap extension as initially described by Ho and coworkers (56). As shown in table 2 the phospholipase A2-like activity of the VP1-unique region could be reduced by exchanging both the tyrosine 157 and 168 to phenylalanine and by the alteration of lysine 162 to leucine. However the exchange of aspartic acid 195 to alanine led to an unexpected enhancement of the activity of the viral enzyme indicating distinct differences between viral and cellular phospholipase A2 enzymes. An almost total destruction of the enzymatic activity could only be achieved by the alteration of histidine 153 to alanine. It can be concluded that this amino acid residue is part of the active centre and most important for the enzymatic activity of the VP1-unique region. Its alteration is associated with the complete destruction of the viral phospholipase A2-like activity.

TABLE 1

Autoimmune diseases that are reported in association to parvovirus B19 infection.

| Involved organs | Disease |
| --- | --- |
| Joints | Arthralgias |
| | Arthritis |
| | Monoarthritis |
| | Oligoarthritis |
| | Polyarthritis |
| | Rheumatoid arthritis |
| | Juvenile idiopathic arthritis |
| Connective tissue/vessels | Systemic lupus erythematosus (SLE) |
| | Vasculitis |
| | Leukoclastic vasculitis |
| | Purpura Henlein-Schoenoch |
| | Papular-purpuric gloves-and-socks syndrome (PPGSS) |
| | Kawasaki disease? |
| | Giant cell arteritis (GCA) |
| | Polyarteritis nodosa |
| | Wegener's granulomatosis |
| | Dermatomyositis |
| Blood cells | Autoimmune neutropenia |
| | Autoimmune thrombocytpenia |
| | Idiopathic thrombocytopenic purpura (ITP) |
| | Autoimmune hemolytic anemia |
| | Virus-associated hemophagocytic syndrome (VAHS) |

TABLE 2

Enzmyatic phopholipase A2-like activity in the VP1-unique region of parvovirus B19 and variants constructed by site-directed mutagenesis.

| Position altered by site-directed mutagenesis | enzyme acitivty (%) |
|---|---|
| wildtype, genotype 1 | 100 |
| active center mutants | |
| histidine 153 → alanine | 0 |
| tyrosine 157 → phenylalanine | 10 |
| lysine 162 → leucine | 61 |
| tyrosine 168 → phenylalanine | 54 |
| aspartic acid 195 → alanine | 204 |
| not-active center mutants | |
| leucine 76 → glutamine, phenylalanine 81 → alanine | 80 |
| isoleucine 66 → leucine, leucine 70 → glutamine | 144 |
| leucine 59 → glutamine, leucine 62 → glutamine | 143 |
| variations in non-conserved regions | |
| parvovirus B19, VP1-unique region genotype 2/strain Berlin ala18→asp, gln21→lys, asn68→ser, asn72→asp, ser73→thr, ser96→pro, ala101→thr, val123→ile, val192→ala | 70 |
| parvovirus B19, VP1-unique region, genotype 3/strain V9 lys4→thr, ser5→thr, gly6→asn, asp12→ser, lys17→gln, ala18→asp, gln21→lys, glu25→gln, val30→ala, asn68→ser, ser98→asn, his100→ser, val123→ile, ser144→asn, val192→ala | 59 |

Example 2

Comparison Study for the Immunogenicity Between Wild Type and Mutant of VP1 Proteins Inoculation of Mice.

Groups of 5 female Balc/C mice were inoculated with 50 ug of purified preparations of the VP1-unique region/wildtype and the VP1-unique region/H153A in emulsion with complete's Freund's Adjuvans. Retrobulbar blood samples were taken at days 0, 3, 7, 10, 14, 18 and 28 after inoculation. The sera were tested for the presence of IgG antibodies against the VP1-unique region/wildtype in ELISA assays.

Protein Production.

The sequences encoding the VP1-unique region/wildtype and the VP1-unique region/H153A were cloned into the T7-expression vector pET21a_int in fusion with an intein and a chitin-binding domain as described previously (Dorsch et al., 2001, Dorsch et al., 2002). The constructs were introduced into the *E. coli* strain BL21. Bacteria were inoculated with LB (luria broth) medium containing 100 μg/ml ampicillin and incubated at 37° C. Expression of the recombinant protein was induced by addition of 1 mM IPTG for at least 3 h of culture. The bacteria were harvested by centrifugation, resuspended in 30 ml 20 mM HEPES, 1 mM EDTA, 100 mM NaCl, pH8.5 and lysed by the use of a French Press. The debris was pelleted at 10000 g. The supernatant was loaded on a chitin column (NEB) using FPLC-system (Pharmacia Biosystems, Freiburg). The column was washed with 2 volumes of 20 mM HEPES, 1 mM EDTA, 100 mM NaCl, pH8.5, 8 volumes of 20 mM HEPES, 1 mM EDTA, 2 mM NaCl, pH8.5 and 2 volumes of 20 mM HEPES, 1 mM EDTA, 100 mM NaCl, pH8.5. Afterwards the protein was eluted using 3 volumes of 50 mM DTT in buffer 20 mM HEPES, 1 mM EDTA, 100 mM NaCl, pH8.5. Fractions were tested for the recombinant proteins by SDS-PAGE and silver staining. Positive fractions were unified and concentrated by using a Centriplus concentrator (3 kD exclusion volume; Amicon, Beverly, USA). The protein concentration was determined after dialysis against PBS (0.9 mM $KH_2PO_4$, 8.0 mM $Na_2HPO_2 \times 12H_2O$, 2.7 mM KCl, 137 mM NaCl) using a Bradford assay (Bio Rad Laboratories, Hercules, USA).

ELISA-Assay.

Microtiter plates (Maxisorb, Nunc, Wiesbaden, FRG) were coated over night with purified protein (VP1-unique region/wildtype, 100 ng/well) in 0.2 M $NaCO_3$ buffer, pH 9.2 containing 0.15 M NaCl. Sera were used in dilutions of 1:100 in PBS/0.5% Tween-20 and IgG-antibodies were detected using HRP-coupled polyclonal rabbit anti-mouse IgG as second antibodies (dilution 1:5000 in PBS/0.5% Tween-20, Dako, Hamburg FRG) and TMB as substrate, the optical density was determined at 450 nm.

Results

Starting from day 7 after inoculation IgG antibodies directed against the VP1-unique region/wildtype were detectable in mice that had been inoculated both with purified preparations of the VP1-unique region/wildtype and the VP1-unique region/H153A (FIG. 1). The amounts of antibodies continually increased until day 28 after inoculation. Differences in the reactivity of mice inoculated with either the VP1-unique region/wildtype or the VP1-unique region/H153A could not be observed. These results indicate that both proteins are highly antigenic. Antibodies induced against the variant VP1-unique region/H153A have the capacity to bind to the VP1-unique region/wildtype which had used as antigen in the ELISA indicating an high degree of cross reactivity. Mice that were inoculated with PBS in emulsion with complete Freund's adjuvans did not develop any significant amounts of VP1-specific antibodies.

The wildtype VP1-unique region antigen and the mutant antigen (His153Ala) were inoculated in mice. VP1-specific antibody production was analysed by ELISA. No differences were observed in the capacity of both antigens to elicit VP1-specific antibody production. Antibodies against the mutant antigen His153Ala were similarly active to bind to the wildtype VP1-unique region and vice versa. This indicates that the mutant His153Ala variant of the VP1-unique region of parvovirus B19 has a comparable capacity to elicit the production of antibodies as the wildtype protein domain. Since the main neutralising epitopes are known to be located in protein parts different from the active centre of the viral phospholipase A2-like enzyme and were not affects by any of the introduced mutations effects on the protein's immunogenicity are unlikely (57).

The combination of both approaches—the production VP1/VP2-capsids in recombinant *S. cerevisiae* and the destruction of the phospholipase A2-like activity—has the potential to produce a vaccine that allows the prevention of parvovirus B19 infection without a reduced number of side effects due to elevated leukotriene and prostaglandin production and without the dangerous potential to induce autoimmune reactions that may result in life-long rheumatic disease.

Legend

FIG. 1. The development of IgG-antibodies against the VP1-unique region/wildtype. Groups of 5 mice were inoculated with either the VP1-unique region/wildtype, the VP1-unique region/H153A or PBS. Serum samples taken at days after inoculation as indicated were tested in ELISA using the VP1-unique region as antigen. Average values obtained from testing the individual samples of 5 mice were determined in each case.

REFERENCES

1. Cossart Y. E., Cant B., Field A. M., Widdows D. 1975, Lancet 1, 72.
2. Paver W. K., Clarke S. K. R. 1976, J. Clin. Microbiol. 4, 67.
3. Shneerson J. M., Mortimer P P., Vandervelde E. M. 1980, Br. Med. J., 280, 1580.
4. Anderson M., Lewis E., Kidd I. M., Hall S. M., Cohen B. J. 1984, J. Hyg. (London) 93, 85.
5. Chorba T., Coccia P., Holman R. C., Tattersall P., Anderson L. J., Sudman J., Young, N. S., Kurczynski E., Saarinen U. M., Moir R. 1986, J. Infect. Dis. 154, 383.
6. Blümel J., Schmidt I., Effenberger W., Seitz H., Willkommen H., Brackmann H. H., Lo J., Eis-Hübinger A. M. 2002, Transfusion, 42, 1473.
7. Hayakawa F., Imada K., Towatari M., Saito H. 2002, Br. J. Haematol., 118, 1187.
8. Prowse C, Ludlam C. A., Yap P. L. 1997, Vox Sanguinis, 72, 1.
9. Yaegashi N., Niinuma T., Chisaka H., Watanabe T., Uehara S., Okamura K., Moffat S., Sugamura K., Yajima A. 1998, 37, 28.
10. Ozawa K., Young N. 1987, J. Virol., 62, 2508.
11. Brown K. E., Anderson S. M., Young N. S. 1993, Science, 262, 114.
12. Bültmann B. D., Klingel K., Sotlar K., Bock, C. F., Kandolf R. 2003, Virchows Arch. 442, 8.
13. Cassinotti P., Siegl G., Michel B. A., Bruhlmann P. 1998 J. Med. Virol., 56, 199.
14. Eis-Hübinger A. M., Reber U., Abdul-Nour T., Glatzel U., Lauschke H., Putz U. 2001, J. Med. Virol.; 65, 395.
15. Hokynar K., Brunstein J., Söderlund-Venermo M., Kiviluoto O., Partio E. K., Konttinen Y., Hedman K. 2000, J. Gen. Virol., 81, 1017.
16. Söderlund M., von Essen R., Haapasaari J., Kiistala U., Kiviluoto O., Hedman K. 1997, Lancet 349, 1063.
17. Vuorinen T., Lammintausta K., Kotilainen P., Nikkari S. 2002 J. Clin. Virol., 25, 217.
18. Cherry J. D. 1994, Adv. Pediatr., 46, 245.
19. Török T. J. 1997, Anderson L J, Young N S (Ed). Human parvovirus B19. Monogr Virol, Vol. 20. Basel: Karger; 61.
20. Heegard E. D., Brown K. E. 2002, Clin. Microbiol. Rev. 15, 485.
21. Langnas A. N., Markin R. S., Cattral M. S., Naides S. J. 1995, Hepatology 22, 1661
22. Bousvaros A., Sundel R., Thorne G. M., McIntosh K., Cohen M., Erdman D. D., Perez-Atayde A., Finkel T. H., Colin A. A. 1998, Pediatr. Pulmonol. 26, 365.
23. Wardeh A., Marik P. 1998, J. Internal Med., 244, 257.
24. Yoto Y., Kudoh T., Haseyama K., Tsutsumi H. 2001, Lancet, 358, 2168.
25. Rogers B. B., Singer, D. B., Mak S. K., Gary G. W., Fikrig M. K., McMillan P. M. 1993, Obstet. Gynecol. 81, 402.
26. Nyman M., Tolfvenstam T., Petersson K., Krassny C., Skjoldebrand-Sparre L., Broliden K. 2002, Obstet. Gynecol. 99, 795.
27. Miller E., Fairley C. K., Cohen, B. J., Seng C. 1998, B. J. Obstet. Gynaecol. 105, 174.
28. Knöll A., Louwen F., Kochanowski B., Plentz A., Stüssel J., Beckenlehner K., Jilg W., Modrow S. 2002, J. Med. Virol. 67, 259.
29. Kurtzman G. J., Ozawa K., Cohen B., Hanson G., Oseas R., Blase R. M., Young N. S. 1987, N. Engl. J. Med. 317, 287.
30. Pont J., Puchhammer-Stöckl E., Chott A., Popow-Kraupp T., Kienzer I., Postner G., Honetz N. 1992, Br. J. Haematol. 80, 160.
31. Scheurlen W., Ramasubbu K., Wachowski O., Hemauer A., Modrow S. 2001, J. Clin. Virol., 20, 173.
32. Hanada T., Koike K., Hirano C., Takeya T., Suzuki T., Matsunaga Y., Takita H. 1989, Eur. J. Haematol., 42, 77.
33. Lefrere J. J., Courouce A. M., Kaplan C. 1989 Lancet, 1, 279.
34. Murray J. C., Kelley P. K., Hogrefe W. R., McClain K. L. 1994, Am. J. Pediatr. Hematol. Oncol., 16, 314.
35. Hida M., Shimamura J., Ueno E., Watanabe 2000, J. Pediatr. Int., 42, 708.
36. Naides S. J., Scharosch L. L. Foto F., Howard E. J. 1990, Arthritis. Rheum. 33, 1297.
37. Murai C., Munakata Y., Takahashi Y.; Ishii T., Shibata S., Muryoi T., Funato T., Nakamura M., Sugamua K., Sasaki F. T. 1999, Ann. Rheum. Dis 58, 130.
38. Nikkari S., Luukkainen R., Möttönen T., Meurman O., Hannonen P., Skurnik M., Toivanen P. 1994, Ann. Rheum. Dis. 53, 106.
39. Moore T. L. 2000, Curr. Opin. Rheumatol. 12, 289.
40. Lehmann H. W., Kühner L., Beckenlehner K., Müller-Godeffroy E., Heide K. G., Küster R. M., Modrow S. 2002, J. Clin. Virol., 25, 135.
41. Nocton J. J., Miller L. C., Tucker L. B., Schaller J. G. 1993, J. Pediat., 122, 186.
42. Mimori A., Misaki Y., Hachiya T., Ito K., Kano S. 1994, Rheum. Int., 14, 87.
43. Oguz F., Akdeniz C., Unuvar E., Kucukbasmaci O., Sidal M. 2002, J. Paediatr. Child Health 38, 358.
44. Lehmann H. W., Knöll A., Küster R. M., Modrow S. 2003, Arthritis Rheum. 48, 1631.
45. Negro A., Regolisti G., Perazzoli F., Coghi P., Tumiati B., Rossi E. 2001, Ann. Ital. Med. Int., 16, 125.
46. Tovari E., Mezey I., Hedman K., Czirjak L. 2002, Ann. Rheum. Dis., 61, 662.
47. Cope A. P., Jones A., Brozovic M., Shafi M. S., Maini R. N. 1992, Ann. Rheum. Dis., 51, 803.
48. Trapani S., Ermini M., Falcini F. 1999, Semin. Arthr. Rheum. 28, 319.
49. Hemauer A., Beckenlehner K., Wolf H., Lang B., Modrow S. 1999, J. Clin. Virol., 14, 73.
50. Hsu T.-C., Tsay G. J. 2001, Rheumatol., 40, 152.
51. Diaz F., Collazos J., Mendoza F., de la Viuda J. M., Cazallas J., Urkijo J. C., Flores M. 2002, Clin Microbiol Infect., 8, 115.
52. Landenberg v. P., Lehmann H. W., Knöll A., Dorsch S., Modrow S. 2003, Arthritis Rheum. 48, in press.
53. Cervera R., Piette J. C., Font J., Khamashta M. A., Shoenfeld Y., Camps M. T., Jacobsen S., Lakos G., Tincani A., Kontopoulou-Griva I., Galeazzi M., Meroni P. L., Derksen R. H., de Groot P. G., Grommnica-Ihle E., Baleva M., Mosca M., Bombardieri dez-Nebro A., Boffa M. C., Hughes G. R., Ingelmo M. 2002, Arthritis Rheum., 46, 1019.
54. Dorsch S., Liebisch G., Kaufmann B., von Landenberg P., Hoffmann J. H., Drobnik W., Modrow S. 2002, J. Virol. 76, 2014.
55. Ballou W. R., Reed, J. L., Noble, W., Young N. S. 2003, J. Infect. Diseases, 187, 675.
56. Ho S, N., Hunt H. D., Horton R. M., Pullen J. K., Pease L. R. 1989, Gene 77, 51.

57. Gigler A., Dorsch S., Hemauer A., Williams C., Young N. S., Zolla-Pazner S., Gorny M. K., Modrow S. 1999, J. Virol., 73, 1974.

58. Arni R. K., and R. J. Ward. 1996. Phospholipase A2—a structural review. Toxicon 34: 827-841.

59. Moore, T. L., R. Bandlamudi, S. M. Alam, and G. Nesher. 1999. Parvovirus infection mimicking systemic lupus erythematosus in a pediatric population. Semin. Arthritis Rheum. 28: 314-318.

60. Servant A, Laperche S, Lallemand F, Marinho V, De Saint Maur G, Meritet J F, Garbarg-Chenon A. Genetic diversity within human erythroviruses: identification of three genotypes. J. Virol. 2002 76:9124-34.

61. Liefeldt, L., Plentz, A., Klempa, B., Kershaw, O., Endres, A. S., Raab, U., Neumayer, H. H., Meisel, Hans G. Faβbender, H., Modrow, S. Recurrent high level parvovirus B19/genotype 2 viremia in a renal transplant recipient analyzed by real-time PCR for simultaneous detection of genotypes 1 to 3. J. Med. Virol., in press.

62. Dorsch, S., Kaufmann, B., Schaible, U., Prohaska, E., Wolf, H., Modrow, S. (2001) The VP1-unique region of parvovirus B19: Amino acid variability and antigenic stability. J. Gen. Virol., 82, 191-199.

63. Dorsch, S., Liebisch, G., Kaufmann, B., Hoffmann, J. H., v. Landenberg, P., Dropnik, W., Modrow, S. (2002) The VP1-unique region of parvovirus B19 and its constituent phospholipase A2-like activity. J. Virol., 76, 2014-2018.

The invention claimed is:

1. A pharmaceutical composition comprising a modified VP1-capsid protein of parvovirus B19, wherein a wild type sequence of the VP-1 capsid protein has been modified to contain amino acid substitutions at positions corresponding to histidine 153 of SEQ ID NO:1, tyrosine 157 of SEQ ID NO:1, lysine 162 of SEQ ID NO:1, and tyrosine 168 of SEQ ID NO:1, wherein said substitutions are histidine 153 to alanine, tyrosine 157 to phenylalanine, lysine 162 to leucine, and tyrosine 168 to phenylalanine, and wherein said modified VP1-capsid protein has a reduced phospholipase A2 enzyme activity as compared to the wild type VP1-capsid protein.

2. The pharmaceutical composition of claim 1, further comprising a carrier or adjuvant suitable for vaccination purposes.

3. The pharmaceutical composition of claim 1, further comprising an immunostimulatory substance selected from the group consisting of an immunostimulatory deoxynucleotide (ODN), a peptide containing at least two LysLeuLys motifs, a neuroactive compound, alum, Freund's complete adjuvant, and Freund's incomplete adjuvant.

4. The pharmaceutical composition of claim 1, further comprising a polycationic peptide.

5. The pharmaceutical composition of claim 1, further comprising a VP2-capsid protein.

6. The pharmaceutical composition of claim 5, wherein the modified VP1-capsid protein is fused to the VP2-capsid protein.

7. A pharmaceutical composition comprising (a) an adjuvant, and (b) a modified VP1-capsid protein of parvovirus B19, wherein a wild type sequence of the VP1-capsid protein of parvovirus B19 has been modified to contain an amino acid substitution at a position corresponding to tyrosine 157 of SEQ ID NO: 1, lysine 162 of SEQ ID NO: 1, or tyrosine 168 of SEQ ID NO: 1, wherein said substitution is selected from the group consisting of tyrosine 157 to phenylalanine, lysine 162 to leucine, and tyrosine 168 to phenylalanine; and wherein said modified VP1-capsid protein has a reduced phospholipase A enzyme activity as compared to the wild type VP1-capsid protein.

8. The pharmaceutical composition of claim 7, wherein the substitution is lysine 162 to leucine.

9. The pharmaceutical composition of claim 7, wherein the substitution is tyrosine 168 to phenylalanine.

10. The pharmaceutical composition of claim 7, wherein the substitution is tyrosine 157 to phenylalanine.

11. The pharmaceutical composition of claim 7, wherein said adjuvant is an immunostimulatory substance selected from the group consisting of an immunostimulatory deoxynucleotide (ODN), a peptide containing at least two LysLeuLys motifs, a neuroactive compound, alum, Freund's complete adjuvant, and Freund's incomplete adjuvant.

12. The pharmaceutical composition of claim 7, further comprising a polycationic peptide.

13. The pharmaceutical composition of claim 7, further comprising a VP2-capsid protein.

14. The pharmaceutical composition of claim 13, wherein the modified VP1-capsid protein is fused to the VP2-capsid protein.

15. The pharmaceutical composition of claim 1, wherein said wild type VP1-capsid protein has a sequence selected from SEQ ID NO:1, SEQ ID NO:2, and SEQ ID NO:3.

16. The pharmaceutical composition of claim 7 where said wild type VP1-capsid protein has a sequence selected from SEQ ID NO:1, SEQ ID NO:2, and SEQ ID NO:3.

* * * * *

SEQUENCE LISTING

```
<160> NUMBER OF SEQ ID NOS: 9

<210> SEQ ID NO 1
<211> LENGTH: 781
<212> TYPE: PRT
<213> ORGANISM: Parvovirus B19

<400> SEQUENCE: 1

Met Ser Lys Lys Ser Gly Lys Trp Trp Glu Ser Asp Asp Lys Phe Ala
1               5                   10                  15

Lys Ala Val Tyr Gln Gln Phe Val Glu Phe Tyr Glu Lys Val Thr Gly
            20                  25                  30

Thr Asp Leu Glu Leu Ile Gln Ile Leu Lys Asp His Tyr Asn Ile Ser
        35                  40                  45

Leu Asp Asn Pro Leu Glu Asn Pro Ser Ser Leu Phe Asp Leu Val Ala
    50                  55                  60

Arg Ile Lys Asn Asn Leu Lys Asn Ser Pro Asp Leu Tyr Ser His His
65                  70                  75                  80

Phe Gln Ser His Gly Gln Leu Ser Asp His Pro His Ala Leu Ser Ser
                85                  90                  95

Ser Ser Ser His Ala Glu Pro Arg Gly Glu Asn Ala Val Leu Ser Ser
            100                 105                 110

Glu Asp Leu His Lys Pro Gly Gln Val Ser Val Gln Leu Pro Gly Thr
        115                 120                 125

Asn Tyr Val Gly Pro Gly Asn Glu Leu Gln Ala Gly Pro Pro Gln Ser
    130                 135                 140

Ala Val Asp Ser Ala Ala Arg Ile His Asp Phe Arg Tyr Ser Gln Leu
145                 150                 155                 160

Ala Lys Leu Gly Ile Asn Pro Tyr Thr His Trp Thr Val Ala Asp Glu
                165                 170                 175

Glu Leu Leu Lys Asn Ile Lys Asn Glu Thr Gly Phe Gln Ala Gln Val
            180                 185                 190

Val Lys Asp Tyr Phe Thr Leu Lys Gly Ala Ala Ala Pro Val Ala His
        195                 200                 205

Phe Gln Gly Ser Leu Pro Glu Val Pro Ala Tyr Asn Ala Ser Glu Lys
    210                 215                 220

Tyr Pro Ser Met Thr Ser Val Asn Ser Ala Glu Ala Ser Thr Gly Ala
225                 230                 235                 240

Gly Gly Gly Gly Ser Asn Ser Val Lys Ser Met Trp Ser Glu Gly Ala
                245                 250                 255

Thr Phe Ser Ala Asn Ser Val Thr Cys Thr Phe Ser Arg Gln Phe Leu
            260                 265                 270
```

-continued

```
Ile Pro Tyr Asp Pro Glu His His Tyr Lys Val Phe Ser Pro Ala Ala
        275                 280                 285

Ser Ser Cys His Asn Ala Ser Gly Lys Glu Ala Lys Val Cys Thr Ile
    290                 295                 300

Ser Pro Ile Met Gly Tyr Ser Thr Pro Trp Arg Tyr Leu Asp Phe Asn
305                 310                 315                 320

Ala Leu Asn Leu Phe Phe Ser Pro Leu Glu Phe Gln His Leu Ile Glu
                325                 330                 335

Asn Tyr Gly Ser Ile Ala Pro Asp Ala Leu Thr Val Thr Ile Ser Glu
            340                 345                 350

Ile Ala Val Lys Asp Val Thr Asp Lys Thr Gly Gly Gly Val Gln Val
        355                 360                 365

Thr Asp Ser Thr Thr Gly Arg Leu Cys Met Leu Val Asp His Glu Tyr
    370                 375                 380

Lys Tyr Pro Tyr Val Leu Gly Gln Gly Gln Asp Thr Leu Ala Pro Glu
385                 390                 395                 400

Leu Pro Ile Trp Val Tyr Phe Pro Pro Gln Tyr Ala Tyr Leu Thr Val
                405                 410                 415

Gly Asp Val Asn Thr Gln Gly Ile Ser Gly Asp Ser Lys Lys Leu Ala
            420                 425                 430

Ser Glu Glu Ser Ala Phe Tyr Val Leu Glu His Ser Ser Phe Gln Leu
        435                 440                 445

Leu Gly Thr Gly Gly Thr Ala Ser Met Ser Tyr Lys Phe Pro Pro Val
    450                 455                 460

Pro Pro Glu Asn Leu Glu Gly Cys Ser Gln His Phe Tyr Glu Met Tyr
465                 470                 475                 480

Asn Pro Leu Tyr Gly Ser Arg Leu Gly Val Pro Asp Thr Leu Gly Gly
                485                 490                 495

Asp Pro Lys Phe Arg Ser Leu Thr His Glu Asp His Ala Ile Gln Pro
            500                 505                 510

Gln Asn Phe Met Pro Gly Pro Leu Val Asn Ser Val Ser Thr Lys Glu
        515                 520                 525

Gly Asp Ser Ser Asn Thr Gly Ala Gly Lys Ala Leu Thr Gly Leu Ser
    530                 535                 540

Thr Gly Thr Ser Gln Asn Thr Arg Ile Ser Leu Arg Pro Gly Pro Val
545                 550                 555                 560

Ser Gln Pro Tyr His His Trp Asp Thr Asp Lys Tyr Val Thr Gly Ile
                565                 570                 575

Asn Ala Ile Ser His Gly Gln Thr Thr Tyr Gly Asn Ala Glu Asp Lys
            580                 585                 590

Glu Tyr Gln Gln Gly Val Gly Arg Phe Pro Asn Glu Lys Glu Gln Leu
        595                 600                 605

Lys Gln Leu Gln Gly Leu Asn Met His Thr Tyr Phe Pro Asn Lys Gly
    610                 615                 620

Thr Gln Gln Tyr Thr Asp Gln Ile Glu Arg Pro Leu Met Val Gly Ser
625                 630                 635                 640

Val Trp Asn Arg Arg Ala Leu His Tyr Glu Ser Gln Leu Trp Ser Lys
                645                 650                 655

Ile Pro Asn Leu Asp Asp Ser Phe Lys Thr Gln Phe Ala Ala Leu Gly
            660                 665                 670

Gly Trp Gly Leu His Gln Pro Pro Pro Gln Ile Phe Leu Lys Ile Leu
        675                 680                 685

Pro Gln Ser Gly Pro Ile Gly Gly Ile Lys Ser Met Gly Ile Thr Thr
```

-continued 690 695 700

Leu Val Gln Tyr Ala Val Gly Ile Met Thr Val Thr Met Thr Phe Lys
705 710 715 720

Leu Gly Pro Arg Lys Ala Thr Gly Arg Trp Asn Pro Gln Pro Gly Val
725 730 735

Tyr Pro Pro His Ala Ala Gly His Leu Pro Tyr Val Leu Tyr Asp Pro
740 745 750

Thr Ala Thr Asp Ala Lys Gln His His Arg His Gly Tyr Glu Lys Pro
755 760 765

Glu Glu Leu Trp Thr Ala Lys Ser Arg Val His Pro Leu
770 775 780

<210> SEQ ID NO 2
<211> LENGTH: 781
<212> TYPE: PRT
<213> ORGANISM: Parvovirus B19

<400> SEQUENCE: 2

Met Ser Lys Lys Ser Asp Lys Trp Trp Glu Ser Asp Asp Lys Phe Ala
1 5 10 15

Lys Asp Val Tyr Lys Gln Phe Val Glu Phe Tyr Glu Lys Val Thr Glu
20 25 30

Thr Asp Leu Glu Leu Ile Gln Ile Leu Lys Asp His Tyr Asn Ile Ser
35 40 45

Leu Asp Asn Pro Leu Glu Asn Pro Ser Ser Leu Phe Asp Leu Val Ala
50 55 60

Arg Ile Lys Ser Asn Leu Lys Asp Thr Pro Asp Leu Tyr Ser His His
65 70 75 80

Phe Gln Ser His Gly Gln Leu Phe Asp His Pro His Ala Leu Ser Pro
85 90 95

Ser Ser Ser His Thr Glu Pro Arg Gly Glu Asp Ala Val Leu Ser Ser
100 105 110

Glu Asp Leu His Lys Pro Gly Gln Val Ser Ile Gln Leu Pro Gly Thr
115 120 125

Asn Tyr Ile Gly Pro Gly Asn Glu Leu Gln Ala Gly Pro Pro Gln Ser
130 135 140

Ala Val Asp Ser Ala Ala Arg Ile His Asp Phe Arg Tyr Ser Gln Leu
145 150 155 160

Ala Lys Leu Gly Ile Asn Pro Tyr Thr His Trp Thr Val Ala Asp Glu
165 170 175

Glu Leu Leu Lys Asn Ile Lys Asn Glu Thr Gly Phe Gln Ala Gln Ala
180 185 190

Val Lys Asp Tyr Phe Thr Leu Lys Gly Ala Ala Ala Pro Val Ala His
195 200 205

Phe Gln Gly Ser Leu Pro Glu Val Pro Ala Tyr Asn Ala Ser Glu Lys
210 215 220

Tyr Pro Ser Met Thr Ser Val Asn Ser Ala Glu Ala Ser Thr Gly Ala
225 230 235 240

Gly Gly Gly Gly Ser Asn Pro Val Lys Ser Met Trp Ser Glu Gly Ala
245 250 255

Thr Phe Thr Ala Asn Ser Val Thr Cys Thr Phe Ser Arg Gln Phe Leu
260 265 270

Ile Pro Tyr Glu Pro Glu His Arg Tyr Lys Val Phe Ser Pro Ala Ala
275 280 285

```
Ser Ser Cys His Asn Ala Ser Gly Lys Glu Ala Lys Val Cys Thr Ile
    290                 295                 300

Ser Pro Ile Met Gly Tyr Ser Thr Pro Trp Arg Tyr Leu Asp Phe Asn
305                 310                 315                 320

Ala Leu Asn Leu Phe Phe Ser Pro Leu Glu Phe Gln His Leu Ile Glu
                325                 330                 335

Asn Tyr Gly Ser Ile Ala Pro Asp Ala Leu Thr Val Thr Ile Ser Glu
            340                 345                 350

Ile Ala Val Lys Asp Val Thr Asp Lys Thr Gly Gly Gly Val Gln Val
        355                 360                 365

Thr Asp Ser Thr Thr Gly Arg Leu Cys Met Leu Val Asp His Glu Tyr
    370                 375                 380

Lys Tyr Pro Tyr Val Leu Gly Gln Gly Gln Asp Thr Leu Ala Pro Glu
385                 390                 395                 400

Leu Pro Ile Trp Val Tyr Phe Pro Pro Gln Tyr Ala Tyr Leu Thr Ala
                405                 410                 415

Gly Asp Val Asn Thr Gln Gly Ile Ser Gly Asp Ser Lys Lys Leu Ala
            420                 425                 430

Ser Glu Glu Ser Ala Phe Tyr Val Leu Glu His Ser Ser Phe Glu Leu
        435                 440                 445

Leu Gly Thr Gly Gly Ser Ala Thr Met Ser Tyr Lys Phe Pro Pro Val
    450                 455                 460

Pro Pro Glu Asn Leu Glu Gly Cys Ser Gln His Phe Tyr Glu Met Tyr
465                 470                 475                 480

Asn Pro Leu Tyr Gly Ser Arg Leu Gly Val Pro Asp Thr Leu Gly Gly
                485                 490                 495

Asp Pro Lys Phe Arg Ser Leu Thr His Glu Asp His Ala Ile Gln Pro
            500                 505                 510

Gln Asn Phe Met Pro Gly Pro Leu Val Asn Ser Val Ser Thr Lys Glu
        515                 520                 525

Gly Asp Thr Ser Asn Thr Gly Ala Gly Lys Ala Leu Thr Gly Leu Ser
    530                 535                 540

Thr Gly Thr Ser Gln Ser Thr Arg Ile Ser Leu Arg Pro Gly Pro Val
545                 550                 555                 560

Ser Gln Pro Tyr His His Trp Asp Thr Asp Lys Tyr Val Thr Gly Ile
                565                 570                 575

Asn Ala Ile Ser His Gly Gln Thr Thr Tyr Gly Asn Ala Glu Asp Lys
            580                 585                 590

Glu Tyr Gln Gln Gly Val Gly Arg Phe Pro Asn Glu Lys Glu Gln Leu
        595                 600                 605

Lys Gln Leu Gln Gly Leu Asn Ile His Thr Tyr Phe Pro Asn Lys Gly
    610                 615                 620

Thr Gln Gln Tyr Thr Asp Gln Ile Glu Arg Pro Leu Met Val Gly Ser
625                 630                 635                 640

Val Trp Asn Arg Arg Ala Leu His Tyr Glu Ser Gln Leu Trp Ser Lys
                645                 650                 655

Ile Pro Asn Leu Asp Asp Ser Phe Lys Thr Gln Phe Ala Ala Leu Gly
            660                 665                 670

Gly Trp Gly Leu His Gln Pro Pro Pro Gln Ile Phe Leu Lys Ile Leu
        675                 680                 685

Pro Gln Ser Gly Pro Ile Gly Gly Ile Lys Ser Met Gly Ile Thr Thr
    690                 695                 700

Leu Val Gln Tyr Ala Val Gly Ile Met Thr Val Thr Met Thr Phe Lys
```

705 710 715 720

Leu Gly Pro Arg Lys Ala Thr Gly Arg Trp Asn Pro Gln Pro Gly Val
725 730 735

Tyr Pro Pro His Ala Ala Gly His Leu Pro Tyr Val Leu Tyr Asp Pro
740 745 750

Thr Ala Thr Asp Ala Lys Gln His His Arg His Gly Tyr Glu Lys Pro
755 760 765

Glu Glu Leu Trp Thr Ala Lys Ser Arg Val His Pro Leu
770 775 780

<210> SEQ ID NO 3
<211> LENGTH: 781
<212> TYPE: PRT
<213> ORGANISM: Parvovirus B19

<400> SEQUENCE: 3

Met Ser Lys Thr Thr Asn Lys Trp Trp Glu Ser Ser Asp Lys Phe Ala
1 5 10 15

Gln Asp Val Tyr Lys Gln Phe Val Gln Phe Tyr Glu Lys Ala Thr Gly
20 25 30

Thr Asp Leu Glu Leu Ile Gln Ile Leu Lys Asp His Tyr Asn Ile Ser
35 40 45

Leu Asp Asn Pro Leu Glu Asn Pro Ser Ser Leu Phe Asp Leu Val Ala
50 55 60

Arg Ile Lys Ser Asn Leu Lys Asn Ser Pro Asp Leu Tyr Ser His His
65 70 75 80

Phe Gln Ser His Gly Gln Leu Ser Asp His Pro His Ala Leu Ser Ser
85 90 95

Ser Asn Ser Ser Ala Glu Pro Arg Gly Glu Asn Ala Val Leu Ser Ser
100 105 110

Glu Asp Leu His Lys Pro Gly Gln Val Ser Ile Gln Leu Pro Gly Thr
115 120 125

Asn Tyr Val Gly Pro Gly Asn Glu Leu Gln Ala Gly Pro Pro Gln Asn
130 135 140

Ala Val Asp Ser Ala Ala Arg Ile His Asp Phe Arg Tyr Ser Gln Leu
145 150 155 160

Ala Lys Leu Gly Ile Asn Pro Tyr Thr His Trp Thr Val Ala Asp Glu
165 170 175

Glu Leu Leu Lys Asn Ile Lys Asn Glu Thr Gly Phe Gln Ala Gln Ala
180 185 190

Val Lys Asp Tyr Phe Thr Leu Lys Gly Ala Ala Ala Pro Val Ala His
195 200 205

Phe Gln Gly Ser Leu Pro Glu Val Pro Ala Tyr Asn Ala Ser Glu Lys
210 215 220

Tyr Pro Ser Met Thr Ser Val Asn Ser Ala Glu Ala Ser Thr Gly Ala
225 230 235 240

Gly Gly Gly Gly Ser Asn Pro Thr Lys Ser Met Trp Ser Glu Gly Ala
245 250 255

Thr Phe Thr Ala Asn Ser Val Thr Cys Thr Phe Ser Arg Gln Phe Leu
260 265 270

Ile Pro Tyr Asp Pro Glu His His Tyr Lys Val Phe Ser Pro Ala Ala
275 280 285

Ser Ser Cys His Asn Ala Ser Gly Lys Glu Ala Lys Val Cys Thr Ile
290 295 300

-continued

```
Ser Pro Ile Met Gly Tyr Ser Thr Pro Trp Arg Tyr Leu Asp Phe Asn
305                 310                 315                 320

Ala Leu Asn Leu Phe Phe Ser Pro Leu Glu Phe Gln His Leu Ile Glu
                325                 330                 335

Asn Tyr Gly Ser Ile Ala Pro Asp Ala Leu Thr Val Thr Ile Ser Glu
            340                 345                 350

Ile Ala Val Lys Asp Val Thr Asp Lys Thr Gly Gly Gly Val Gln Val
        355                 360                 365

Thr Asp Ser Thr Thr Gly Arg Leu Cys Met Leu Val Asp His Glu Tyr
    370                 375                 380

Lys Tyr Pro Tyr Val Leu Gly Gln Gly Gln Asp Thr Leu Ala Pro Glu
385                 390                 395                 400

Leu Pro Ile Trp Val Tyr Phe Pro Pro Gln Tyr Ala Tyr Leu Thr Val
                405                 410                 415

Gly Glu Val Asn Thr Gln Gly Ile Ser Gly Asp Ser Lys Lys Leu Ala
            420                 425                 430

Ser Glu Glu Ser Ala Phe Tyr Val Leu Glu His Ser Ser Phe Glu Leu
        435                 440                 445

Leu Gly Thr Gly Gly Ser Ala Thr Met Ser Tyr Lys Phe Pro Ala Val
    450                 455                 460

Pro Pro Glu Asn Leu Glu Gly Cys Ser Gln His Phe Tyr Glu Met Tyr
465                 470                 475                 480

Asn Pro Leu Tyr Gly Ser Arg Leu Gly Val Pro Asp Thr Leu Gly Gly
                485                 490                 495

Asp Pro Lys Phe Arg Ser Leu Thr His Glu Asp His Ala Ile Gln Pro
            500                 505                 510

Gln Asn Phe Met Pro Gly Pro Leu Ile Asn Ser Val Ser Thr Lys Glu
        515                 520                 525

Gly Asp Asn Ser Asn Thr Gly Ala Gly Lys Ala Leu Thr Gly Leu Ser
    530                 535                 540

Thr Gly Thr Ser Gln Asn Thr Arg Ile Ser Leu Arg Pro Gly Pro Val
545                 550                 555                 560

Ser Gln Pro Tyr His His Trp Asp Thr Asp Lys Tyr Val Thr Gly Ile
                565                 570                 575

Asn Ala Ile Ser His Gly Gln Thr Thr Tyr Gly Asn Ala Glu Asp Lys
            580                 585                 590

Glu Tyr Gln Gln Gly Val Gly Arg Phe Pro Asn Glu Lys Glu Gln Leu
        595                 600                 605

Lys Gln Leu Gln Gly Leu Asn Met His Thr Tyr Phe Pro Asn Lys Gly
    610                 615                 620

Thr Gln Gln Tyr Thr Asp Gln Ile Glu Arg Pro Leu Met Val Gly Ser
625                 630                 635                 640

Val Trp Asn Arg Arg Ala Leu His Tyr Glu Ser Gln Leu Trp Ser Lys
                645                 650                 655

Ile Pro Asn Leu Asp Asp Ser Phe Lys Thr Gln Phe Ala Ala Leu Gly
            660                 665                 670

Gly Trp Gly Leu His Gln Pro Pro Pro Gln Ile Phe Leu Lys Ile Leu
        675                 680                 685

Pro Gln Ser Gly Pro Ile Gly Gly Ile Lys Ser Met Gly Ile Thr Thr
    690                 695                 700

Leu Val Gln Tyr Ala Val Gly Ile Met Thr Val Thr Met Thr Phe Lys
705                 710                 715                 720

Leu Gly Pro Arg Lys Ala Thr Gly Arg Trp Asn Pro Gln Pro Gly Val
```

```
            725                 730                 735

Tyr Pro Pro His Ala Ala Gly His Leu Pro Tyr Val Leu Tyr Asp Pro
        740                 745                 750

Thr Ala Thr Asp Ala Lys Gln His His Arg His Gly Tyr Glu Lys Pro
    755                 760                 765

Glu Glu Leu Trp Thr Ala Lys Ser Arg Val His Pro Leu
770                 775                 780


<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Lys Leu Lys Leu Leu Leu Leu Leu Lys Leu Lys
1               5                   10


<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (1)..(9)
<223> OTHER INFORMATION: X = any positively charged amino acid

<400> SEQUENCE: 5

Xaa Glx Xaa Glx Glx Glx Xaa Glx Xaa
1               5


<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (1)..(10)
<223> OTHER INFORMATION: X = any positively charged amino acid

<400> SEQUENCE: 6

Xaa Glx Xaa Glx Glx Glx Glx Xaa Glx Xaa
1               5                   10


<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (1)..(11)

<400> SEQUENCE: 7

Xaa Glx Xaa Glx Glx Glx Glx Glx Xaa Glx Xaa
1               5                   10
```

-continued

```
<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (1)..(12)
<223> OTHER INFORMATION: X = any positively charged amino acid

<400> SEQUENCE: 8

Xaa Glx Xaa Glx Glx Glx Glx Glx Glx Xaa Glx Xaa
1               5                   10


<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: MOD_RES
<222> LOCATION: (1)..(13)
<223> OTHER INFORMATION: X = any positively charged amino acid

<400> SEQUENCE: 9

Xaa Glx Xaa Glx Glx Glx Glx Glx Glx Glx Xaa Glx Xaa
1               5                   10
```